(12) United States Patent
Nikolic et al.

(10) Patent No.: US 8,827,892 B2
(45) Date of Patent: Sep. 9, 2014

(54) THERAPEUTIC METHODS AND DEVICES FOLLOWING MYOCARDIAL INFARCTION

(71) Applicant: CardioKinetix, Inc., Menlo Park, CA (US)

(72) Inventors: Serjan D. Nikolic, San Francisco, CA (US); Alexander Khairkhahan, Palo Alto, CA (US)

(73) Assignee: CardioKinetix, Inc., Menlo Park, CA (US)

(*) Notice: Subject to any disclaimer, the term of this patent is extended or adjusted under 35 U.S.C. 154(b) by 0 days.

(21) Appl. No.: 13/973,868

(22) Filed: Aug. 22, 2013

(65) Prior Publication Data

US 2013/0338695 A1    Dec. 19, 2013

Related U.S. Application Data

(63) Continuation of application No. 12/129,443, filed on May 29, 2008, now Pat. No. 8,529,430, which is a continuation-in-part of application No. 11/199,633, filed on Aug. 9, 2005, now abandoned, which is a continuation-in-part of application No. 10/212,032, filed on Aug. 1, 2002, now Pat. No. 7,279,007.

(60) Provisional application No. 60/985,171, filed on Nov. 2, 2007.

(51) Int. Cl.
*A61B 17/00* (2006.01)
*A61B 17/12* (2006.01)
*A61F 2/24* (2006.01)

(52) U.S. Cl.
CPC ....... *A61B 17/0057* (2013.01); *A61B 17/12022* (2013.01); *A61B 2017/00632* (2013.01); *A61B 2017/00575* (2013.01); *A61F 2/2487* (2013.01); *A61F 2002/2484* (2013.01); *A61B 17/12172* (2013.01); *A61B 2017/12095* (2013.01); *A61B 2017/00592* (2013.01); *A61B 2017/00243* (2013.01); *A61B 2017/00867* (2013.01); *A61B 17/12122* (2013.01); *A61B 2017/00615* (2013.01)
USPC .......................................................... 600/37

(58) Field of Classification Search
CPC ................. A61B 17/0057; A61B 2017/00575; A61B 2017/00592; A61B 17/12122; A61F 2/2487
USPC .......................................................... 600/37
See application file for complete search history.

(56) References Cited

U.S. PATENT DOCUMENTS 3,874,388 A * 4/1975 King et al. .................... 606/232
4,007,743 A    2/1977 Blake (Continued)

FOREIGN PATENT DOCUMENTS

JP    H08257031 A    10/1996
JP    2003512128 A    4/2003

(Continued)

OTHER PUBLICATIONS

AGA Medical Corporation. www.amplatzer.com/products. "The Muscular VSD Occluder" and "The Septal Occluder" device description. Accessed Apr. 3, 2002.

(Continued)

*Primary Examiner* — Christine Matthews
*Assistant Examiner* — Joshua D Lannu
(74) *Attorney, Agent, or Firm* — Shay Glenn LLP

(57) ABSTRACT

Described herein are methods of treating a patient to prevent or correct cardiac remodeling following myocardial infarction. In general these methods may include inserting or implanting a device in a heart chamber to support the affected region within 72 hours after myocardial infarction. The device may be a support device (e.g., a resilient frame) and/or a partitioning device.

22 Claims, 19 Drawing Sheets

(56) References Cited

U.S. PATENT DOCUMENTS

| | | |
|---|---|---|
| 4,425,908 A | 1/1984 | Simon |
| 4,453,545 A | 6/1984 | Inoue |
| 4,536,893 A | 8/1985 | Parravicini |
| 4,588,404 A | 5/1986 | Lapeyre |
| 4,619,246 A | 10/1986 | Molgaard-Nielsen et al. |
| 4,685,446 A | 8/1987 | Choy |
| 4,710,192 A | 12/1987 | Liotta et al. |
| 4,819,751 A | 4/1989 | Shimada et al. |
| 4,832,055 A | 5/1989 | Palestrant |
| 4,917,089 A | 4/1990 | Sideris |
| 4,983,165 A | 1/1991 | Loiterman |
| 5,104,399 A | 4/1992 | Lazarus |
| 5,192,301 A | 3/1993 | Kamiya et al. |
| 5,192,314 A | 3/1993 | Daskalakis |
| 5,375,612 A | 12/1994 | Cottenceau et al. |
| 5,385,156 A | 1/1995 | Oliva |
| 5,389,087 A | 2/1995 | Miraki |
| 5,425,744 A | 6/1995 | Fagan et al. |
| 5,433,727 A | 7/1995 | Sideris |
| 5,451,235 A | 9/1995 | Lock et al. |
| 5,496,277 A | 3/1996 | Termin et al. |
| 5,527,337 A | 6/1996 | Stack et al. |
| 5,527,338 A | 6/1996 | Purdy |
| 5,549,621 A | 8/1996 | Bessler et al. |
| 5,551,435 A | 9/1996 | Sramek |
| 5,578,069 A | 11/1996 | Miner, II |
| 5,634,936 A | 6/1997 | Linden et al. |
| 5,634,942 A | 6/1997 | Chevillon et al. |
| 5,647,870 A | 7/1997 | Kordis et al. |
| 5,702,343 A | 12/1997 | Alferness |
| 5,709,707 A | 1/1998 | Lock et al. |
| 5,758,664 A | 6/1998 | Campbell et al. |
| 5,791,231 A | 8/1998 | Cohn et al. |
| 5,797,849 A | 8/1998 | Vesely et al. |
| 5,797,960 A | 8/1998 | Stevens et al. |
| 5,800,457 A | 9/1998 | Gelbfish |
| 5,829,447 A * | 11/1998 | Stevens et al. ............... 128/898 |
| 5,833,698 A | 11/1998 | Hinchliffe et al. |
| 5,836,968 A | 11/1998 | Simon et al. |
| 5,843,170 A | 12/1998 | Ahn |
| 5,860,951 A | 1/1999 | Eggers et al. |
| 5,861,003 A | 1/1999 | Latson et al. |
| 5,865,730 A | 2/1999 | Fox et al. |
| 5,865,791 A | 2/1999 | Whayne et al. |
| 5,871,017 A | 2/1999 | Mayer |
| 5,875,782 A | 3/1999 | Ferrari et al. |
| 5,876,325 A | 3/1999 | Mizuno et al. |
| 5,876,449 A | 3/1999 | Starck et al. |
| 5,879,366 A | 3/1999 | Shaw et al. |
| 5,882,340 A | 3/1999 | Yoon |
| 5,910,150 A | 6/1999 | Saadat |
| 5,916,145 A | 6/1999 | Chu et al. |
| 5,924,424 A | 7/1999 | Stevens et al. |
| 5,925,062 A | 7/1999 | Purdy |
| 5,925,076 A | 7/1999 | Inoue |
| 5,928,260 A | 7/1999 | Chin et al. |
| 5,961,440 A | 10/1999 | Schweich, Jr. et al. |
| 5,961,539 A | 10/1999 | Northrup, III et al. |
| 5,984,917 A | 11/1999 | Fleischman et al. |
| 6,024,096 A | 2/2000 | Buckberg |
| 6,024,756 A | 2/2000 | Huebsch et al. |
| 6,036,720 A | 3/2000 | Abrams et al. |
| 6,045,497 A | 4/2000 | Schweich, Jr. et al. |
| 6,059,715 A | 5/2000 | Schweich, Jr. et al. |
| 6,076,013 A | 6/2000 | Brennan et al. |
| 6,077,214 A | 6/2000 | Mortier et al. |
| 6,077,218 A | 6/2000 | Alferness |
| 6,093,199 A | 7/2000 | Brown et al. |
| 6,095,968 A | 8/2000 | Snyders |
| 6,096,347 A | 8/2000 | Geddes et al. |
| 6,099,832 A | 8/2000 | Mickle et al. |
| 6,102,887 A | 8/2000 | Altman |
| 6,125,852 A | 10/2000 | Stevens et al. |
| 6,132,438 A | 10/2000 | Fleischman et al. |
| 6,142,973 A | 11/2000 | Carleton et al. |
| 6,152,144 A | 11/2000 | Lesh et al. |
| 6,155,968 A | 12/2000 | Wilk |
| 6,156,027 A | 12/2000 | West |
| 6,161,543 A | 12/2000 | Cox et al. |
| 6,193,731 B1 | 2/2001 | Oppelt et al. |
| 6,221,092 B1 | 4/2001 | Koike et al. |
| 6,221,104 B1 * | 4/2001 | Buckberg et al. .............. 623/3.1 |
| 6,230,714 B1 | 5/2001 | Alferness et al. |
| 6,231,561 B1 | 5/2001 | Frazier et al. |
| 6,258,021 B1 | 7/2001 | Wilk |
| 6,267,772 B1 | 7/2001 | Mulhauser et al. |
| 6,290,674 B1 | 9/2001 | Roue et al. |
| 6,296,656 B1 | 10/2001 | Bolduc et al. |
| 6,312,446 B1 | 11/2001 | Huebsch et al. |
| 6,328,727 B1 | 12/2001 | Frazier et al. |
| 6,334,864 B1 | 1/2002 | Amplatz et al. |
| 6,343,605 B1 | 2/2002 | Lafontaine |
| 6,348,068 B1 | 2/2002 | Campbell et al. |
| 6,355,052 B1 | 3/2002 | Neuss et al. |
| 6,360,749 B1 * | 3/2002 | Jayaraman ................... 128/898 |
| 6,364,896 B1 | 4/2002 | Addis |
| 6,387,042 B1 | 5/2002 | Herrero |
| 6,406,420 B1 | 6/2002 | McCarthy et al. |
| 6,419,669 B1 | 7/2002 | Frazier et al. |
| 6,436,088 B2 | 8/2002 | Frazier et al. |
| 6,450,171 B1 | 9/2002 | Buckberg et al. |
| 6,482,146 B1 | 11/2002 | Alferness et al. |
| 6,482,228 B1 | 11/2002 | Norred |
| 6,506,204 B2 | 1/2003 | Mazzocchi |
| 6,508,756 B1 | 1/2003 | Kung et al. |
| 6,511,496 B1 | 1/2003 | Huter et al. |
| 6,537,198 B1 | 3/2003 | Vidlund et al. |
| 6,551,303 B1 | 4/2003 | Van Tassel et al. |
| 6,572,643 B1 | 6/2003 | Gharibadeh |
| 6,586,414 B2 | 7/2003 | Haque et al. |
| 6,592,608 B2 | 7/2003 | Fisher et al. |
| 6,613,013 B2 | 9/2003 | Haarala et al. |
| 6,622,730 B2 | 9/2003 | Ekvall et al. |
| 6,645,199 B1 | 11/2003 | Jenkins et al. |
| 6,652,555 B1 | 11/2003 | Van Tassel et al. |
| 6,681,773 B2 | 1/2004 | Murphy et al. |
| 6,685,627 B2 | 2/2004 | Jayaraman |
| 6,702,763 B2 | 3/2004 | Murphy et al. |
| 6,730,108 B2 | 5/2004 | Van Tassel et al. |
| 6,776,754 B1 | 8/2004 | Wilk |
| 6,852,076 B2 | 2/2005 | Nikolic et al. |
| 6,887,192 B1 | 5/2005 | Whayne et al. |
| 6,951,534 B2 | 10/2005 | Girard et al. |
| 6,959,711 B2 | 11/2005 | Murphy et al. |
| 6,994,093 B2 | 2/2006 | Murphy et al. |
| 7,144,363 B2 | 12/2006 | Pai et al. |
| 7,172,551 B2 | 2/2007 | Leasure |
| 7,279,007 B2 | 10/2007 | Nikolic et al. |
| 7,303,526 B2 | 12/2007 | Sharkey et al. |
| 7,320,665 B2 | 1/2008 | Vijay |
| 7,399,271 B2 | 7/2008 | Sharkey et al. |
| 7,485,088 B2 | 2/2009 | Murphy et al. |
| 7,569,062 B1 | 8/2009 | Kuehn et al. |
| 7,582,051 B2 | 9/2009 | Khairkhahan et al. |
| 7,674,222 B2 | 3/2010 | Nikolic et al. |
| 7,762,943 B2 | 7/2010 | Khairkhahan |
| 7,862,500 B2 | 1/2011 | Sharkey et al. |
| 7,887,477 B2 | 2/2011 | Sharkey et al. |
| 7,897,086 B2 | 3/2011 | Khairkhahan et al. |
| 7,938,767 B2 | 5/2011 | Evans et al. |
| 7,976,455 B2 | 7/2011 | Khairkhahan |
| 8,192,478 B2 | 6/2012 | Khairkhahan et al. |
| 8,246,671 B2 | 8/2012 | Khairkhahan et al. |
| 8,257,428 B2 | 9/2012 | Khairkhahan et al. |
| 8,377,114 B2 | 2/2013 | Khairkhahan et al. |
| 8,388,672 B2 | 3/2013 | Khairkhahan et al. |
| 8,398,537 B2 | 3/2013 | Khairkhahan et al. |
| 8,500,790 B2 | 8/2013 | Khairkhahan |
| 8,500,795 B2 | 8/2013 | Khairkhahan et al. |
| 8,529,430 B2 | 9/2013 | Nikolic et al. |
| 2001/0014800 A1 | 8/2001 | Frazier et al. |
| 2002/0019580 A1 | 2/2002 | Lau et al. |
| 2002/0026092 A1 | 2/2002 | Buckberg et al. |
| 2002/0028981 A1 | 3/2002 | Lau et al. |

(56) References Cited

U.S. PATENT DOCUMENTS

| | | |
|---|---|---|
| 2002/0032481 A1 | 3/2002 | Gabbay |
| 2002/0055767 A1 | 5/2002 | Forde et al. |
| 2002/0055775 A1 | 5/2002 | Carpentier et al. |
| 2002/0111647 A1 | 8/2002 | Khairkhahan et al. |
| 2002/0133227 A1 | 9/2002 | Murphy et al. |
| 2002/0161392 A1 | 10/2002 | Dubrul |
| 2002/0161394 A1 | 10/2002 | Macoviak et al. |
| 2002/0169359 A1 | 11/2002 | McCarthy et al. |
| 2002/0169360 A1* | 11/2002 | Taylor et al. .............. 600/37 |
| 2002/0183604 A1 | 12/2002 | Gowda et al. |
| 2002/0188170 A1 | 12/2002 | Santamore et al. |
| 2003/0045896 A1 | 3/2003 | Murphy et al. |
| 2003/0078671 A1 | 4/2003 | Lesniak et al. |
| 2003/0109770 A1 | 6/2003 | Sharkey et al. |
| 2003/0120337 A1 | 6/2003 | Van Tassel et al. |
| 2003/0135230 A1 | 7/2003 | Massey et al. |
| 2003/0149333 A1 | 8/2003 | Alferness |
| 2003/0149422 A1 | 8/2003 | Muller |
| 2003/0181942 A1 | 9/2003 | Sutton et al. |
| 2003/0220667 A1 | 11/2003 | van der Burg et al. |
| 2004/0002626 A1 | 1/2004 | Feld et al. |
| 2004/0034366 A1 | 2/2004 | van der Burg et al. |
| 2004/0044361 A1 | 3/2004 | Frazier et al. |
| 2004/0054394 A1 | 3/2004 | Lee |
| 2004/0064014 A1 | 4/2004 | Melvin et al. |
| 2004/0122090 A1 | 6/2004 | Lipton |
| 2004/0127935 A1 | 7/2004 | Van Tassel et al. |
| 2004/0133062 A1 | 7/2004 | Pai et al. |
| 2004/0136992 A1 | 7/2004 | Burton et al. |
| 2004/0172042 A1 | 9/2004 | Suon et al. |
| 2004/0186511 A1 | 9/2004 | Stephens et al. |
| 2004/0215230 A1 | 10/2004 | Frazier et al. |
| 2004/0260331 A1 | 12/2004 | D'Aquanni et al. |
| 2004/0260346 A1 | 12/2004 | Overall et al. |
| 2004/0267086 A1 | 12/2004 | Anstadt et al. |
| 2004/0267378 A1 | 12/2004 | Gazi et al. |
| 2005/0007031 A1 | 1/2005 | Hyder |
| 2005/0015109 A1 | 1/2005 | Lichtenstein |
| 2005/0038470 A1 | 2/2005 | van der Burg et al. |
| 2005/0043708 A1 | 2/2005 | Gleeson et al. |
| 2005/0065548 A1 | 3/2005 | Marino et al. |
| 2005/0085826 A1 | 4/2005 | Nair et al. |
| 2005/0096498 A1 | 5/2005 | Houser et al. |
| 2005/0113861 A1 | 5/2005 | Corcoran et al. |
| 2005/0124849 A1 | 6/2005 | Barbut et al. |
| 2005/0137690 A1 | 6/2005 | Salahieh et al. |
| 2005/0142180 A1 | 6/2005 | Bisgaier et al. |
| 2005/0177180 A1 | 8/2005 | Kaganov et al. |
| 2005/0187620 A1 | 8/2005 | Pai et al. |
| 2005/0216052 A1 | 9/2005 | Mazzocchi et al. |
| 2005/0228434 A1 | 10/2005 | Amplatz et al. |
| 2005/0277981 A1 | 12/2005 | Maahs et al. |
| 2005/0277983 A1 | 12/2005 | Saadat et al. |
| 2005/0283218 A1 | 12/2005 | Williams |
| 2006/0019888 A1 | 1/2006 | Zhou |
| 2006/0025800 A1 | 2/2006 | Suresh |
| 2006/0030881 A1 | 2/2006 | Sharkey et al. |
| 2006/0063970 A1 | 3/2006 | Raman et al. |
| 2006/0069430 A9 | 3/2006 | Rahdert et al. |
| 2006/0079736 A1 | 4/2006 | Chin et al. |
| 2006/0116692 A1 | 6/2006 | Ward |
| 2006/0199995 A1 | 9/2006 | Vijay |
| 2006/0229491 A1 | 10/2006 | Sharkey et al. |
| 2006/0259124 A1 | 11/2006 | Matsuoka et al. |
| 2006/0276684 A1 | 12/2006 | Speziali |
| 2007/0129753 A1 | 6/2007 | Quinn et al. |
| 2007/0135889 A1 | 6/2007 | Moore et al. |
| 2007/0162048 A1 | 7/2007 | Quinn et al. |
| 2007/0213578 A1 | 9/2007 | Khairkhahan et al. |
| 2007/0213815 A1 | 9/2007 | Khairkhahan et al. |
| 2008/0015717 A1 | 1/2008 | Griffin et al. |
| 2008/0045778 A1 | 2/2008 | Lichtenstein et al. |
| 2008/0228205 A1 | 9/2008 | Khairkhahan et al. |
| 2010/0121132 A1 | 5/2010 | Nikolic et al. |
| 2010/0274227 A1 | 10/2010 | Khairkhahan et al. |
| 2011/0087066 A1 | 4/2011 | Boutillette et al. |
| 2011/0098525 A1 | 4/2011 | Kermode et al. |
| 2011/0178362 A1 | 7/2011 | Evans et al. |
| 2011/0264204 A1 | 10/2011 | Khairkhahan |
| 2013/0090677 A1 | 4/2013 | Evans et al. |
| 2013/0165735 A1 | 6/2013 | Khairkhahan et al. |
| 2013/0270735 A1 | 10/2013 | Alexander |
| 2013/0274595 A1 | 10/2013 | Kermode et al. |

FOREIGN PATENT DOCUMENTS

| | | |
|---|---|---|
| JP | 2003512129 A | 4/2003 |
| JP | 2005324019 | 11/2005 |
| WO | WO 96/37859 A1 | 11/1996 |
| WO | WO 98/03213 A1 | 1/1998 |
| WO | WO 00/27292 | 5/2000 |
| WO | WO 00/42919 A1 | 7/2000 |
| WO | WO 00/50639 A2 | 8/2000 |
| WO | WO 01/30266 | 5/2001 |
| WO | WO 01/78625 | 10/2001 |
| WO | WO 02/30335 | 4/2002 |
| WO | WO 02/45710 A1 | 6/2002 |
| WO | WO 02/071977 A2 | 9/2002 |
| WO | WO 02/087481 A1 | 11/2002 |
| WO | WO 03/007778 | 1/2003 |
| WO | WO 03/043507 A2 | 5/2003 |
| WO | WO 03/073961 A1 | 9/2003 |
| WO | WO 03/090716 A1 | 11/2003 |
| WO | WO 03/099300 A1 | 12/2003 |
| WO | WO 03/099320 A1 | 12/2003 |
| WO | WO 03/103538 A1 | 12/2003 |
| WO | WO 03/103743 A2 | 12/2003 |
| WO | WO 2004/012629 | 2/2004 |
| WO | WO 2004/019866 A2 | 3/2004 |
| WO | WO 2004/066805 A2 | 8/2004 |
| WO | WO 2004/100803 A1 | 11/2004 |
| WO | WO 2005/007031 | 1/2005 |
| WO | WO 2005/007873 A2 | 1/2005 |
| WO | WO 2005/041745 A2 | 5/2005 |
| WO | WO 2005/091860 A2 | 10/2005 |
| WO | WO 2005/102181 A1 | 11/2005 |
| WO | WO 2006/033107 A2 | 3/2006 |
| WO | WO 2007/092354 | 8/2007 |
| WO | WO 2007/143560 A2 | 12/2007 |

OTHER PUBLICATIONS

Artrip et al.; Left ventricular volume reduction surgery for heart failure: A physiologic perspective; J Thorac Cardiovasc Surg; vol. 122; No. 4; pp. 775-782; Oct. 2001.

Boersma et al.; Early thrombolytic treatment in acute myocardial infarction: reappraisal of the golden hour; Lancet; vol. 348(9030); pp. 771-775; Sep. 21, 1996.

Di Mattia, et al. Surgical treatment of left ventricular post-infarction aneurysm with endoventriculoplasty: late clinical and functioal results. European Journal of Cardio-thoracic Surgery. 15(4):413-418; Apr. 1999.

Dor, et al. Ventricular remodeling in coronary artery disease. Current Opinion in Cardiology. 12(6):533-537; Nov. 1997.

Dor, V. The treatment of refractory ischemic ventricular tachycardia by endoventricular patch plasty reconstruction of the left ventricle. Seminars in Thoracic and Cardiovascular Surgery. 9(2): 146-155; Apr. 1997.

Dor. Surgery for left ventricular aneurysm. Current Opinion in Cardiology. vol. 5; No. 6; pp. 773-780; Dec. 1990.

Gore Medical. www.goremedical.com. "Helex Septal Occluder" product description. Accessed Apr. 3, 2002.

James et al.; Blood Volume and Brain Natriuretic Peptide in Congestive Heart Failure: A Pilot Study; American Heart Journal; vol. 150; issue 5, pp. 984.e1-984.e6 (abstract); Dec. 6, 2005.

Januzzi, James L.; Natriuretic peptide testing: A window into the diagnosis and prognosis of heart failure; Cleveland Clinic Journal of Medicine; vol. 73; No. 2; pp. 149-152 and 155-157; Feb. 2006.

(56) References Cited

OTHER PUBLICATIONS

Katsumata, et al. An objective appraisal of partial left ventriculectomy for heart failure. Journal of Congestive Heart Failure and Circulator Support. 1(2): 97-106; (year of pub. sufficiently earlier than effective US filing date and any foreign priority date) 1999.

Kawata, et al. Systolic and Diastolic Function after Patch Reconstruction of Left Ventricular Aneurysms. Ann. Thorac. Surg. 5(2)9:403-407; Feb. 1995.

Sharkey et al.; Left ventricular apex occluder. Description of a a ventricular partitioning device; EuroInterv.; 2(1); pp. 125-127; May 2006.

U.S. Food & Drug Administration; AneuRx Stent Graft System—Instructions for use; (pre-market approval); Sep. 29, 1999; downloaded Apr. 25, 2013 (http://www.accessdata.fda.gov/cdrh_docs/pdf/P990020c.pdf).

Khairkhahan, Alexander; U.S. Appl. No. 113/954,221 entitled "Retrievable Cardiac Devices," filed Jul. 30, 2013.

* cited by examiner

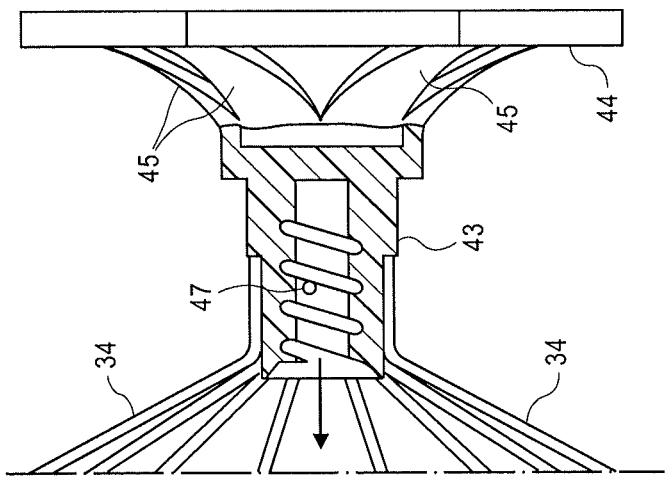
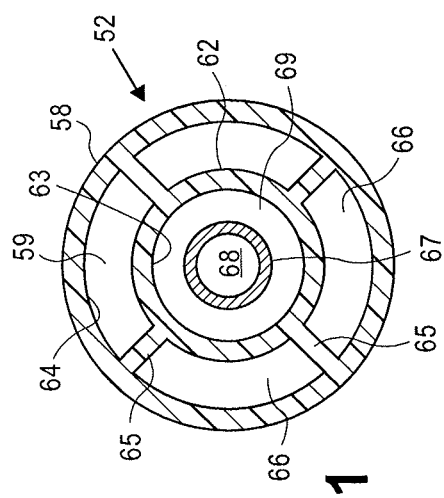
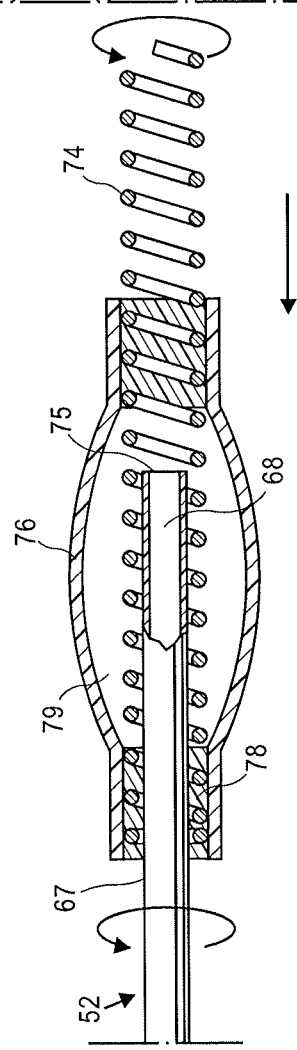
FIG. 11
FIG. 12

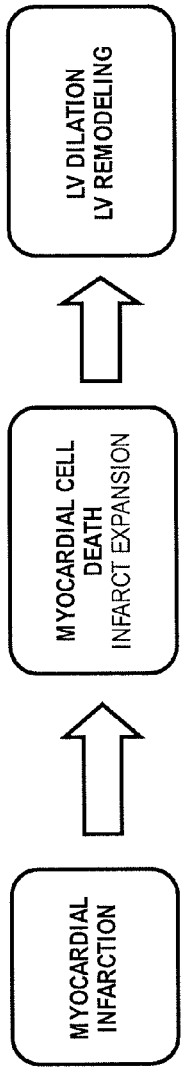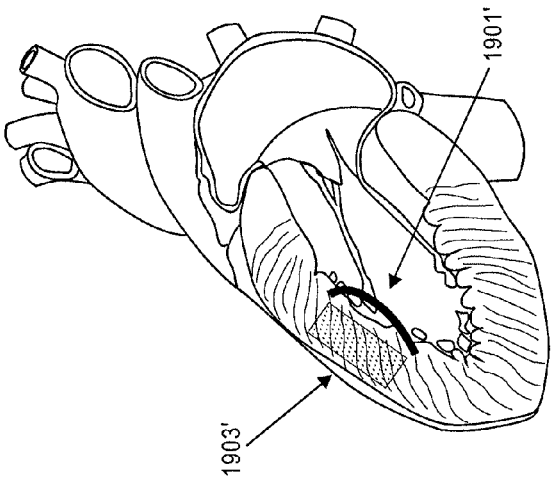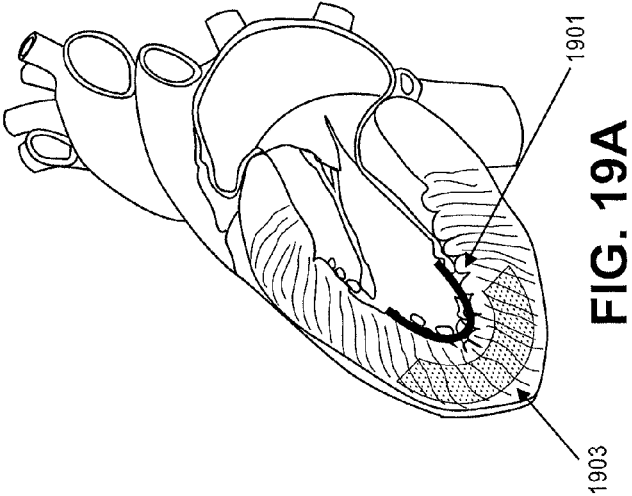
FIG. 18
FIG. 19A
FIG. 19B

THERAPEUTIC METHODS AND DEVICES FOLLOWING MYOCARDIAL INFARCTION

CROSS-REFERENCE TO RELATED APPLICATIONS

This application claims priority as a continuation of U.S. patent application Ser. No. 12/129,443, filed on May 29, 2008, titled "THERAPEUTIC METHODS AND DEVICES FOLLOWING MYOCARDIAL INFARCTION," now U.S. Patent Application Publication No. 2008-0319254-A1, which is a continuation-in-part of U.S. patent application Ser. No. 11/199,633, filed on Aug. 9, 2005, titled "METHOD FOR TREATING MYOCARDIAL RUPTURE," now U.S. Patent Application Publication No. 2006-0229491-A1, now abandoned, which is a continuation-in-part of U.S. application Ser. No. 10/212,032, filed on Aug. 1, 2002, titled "METHOD FOR IMPROVING CARDIAC FUNCTION," now U.S. Pat. No. 7,279,007, each of which is herein incorporated by reference in its entirety.

U.S. patent application Ser. No. 12/129,443 also claims priority to U.S. Provisional Patent Application No. 60/985,171, filed on Nov. 2, 2007, titled "ENDOCARDIAL DEVICE FOR IMPROVING CARDIAC FUNCTION," which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference

BACKGROUND

The present invention relates generally to the field of treating heart disease, particularly preventing remodeling following myocardial infarction.

When normal blood supply to myocardium is stopped due to occluded coronary artery, affected heart muscle cells get severely damaged and/or die, i.e. the myocardium (heart muscle) becomes infracted. This may result in permanent damage to the heart, reduced effectiveness of the heart pumping ability, and is frequently followed by enlargement of the heart and symptoms of heart failure.

An acute myocardial infarction (AMI) may lead to severe myocardial damage resulting in myocardial rupture. Mortality rates for myocardial rupture are extremely high unless early diagnosis and surgical intervention are provided rapidly. Cardiac rupture is a medical emergency. The overall risk of death depends on the speed of the treatment provided, therefore fast and relatively easy treatment option is needed.

Myocardial regions affected by infarction may change size and shape, i.e. remodels, and in many cases non-affected myocardium remodels as well. The infracted region expands due to the forces produced by the viable myocardium. Whether these changes become permanent and progress to involve infracted border zones and remote non-infarcted myocardium may depend on multiple factors, including infarct size, promptness of reperfusion, post-infarction therapy, etc. However, even following small infarction, many patients treated with the state-of-the-art therapies show some degree of regional and subsequent global ventricular shape changes and enlargement. Early infarct expansion results from degradation of the extracellular collagen framework that normally provides myocardial cells coupling and serves to optimize and evenly distribute force development within the ventricular walls. In the absence of extracellular matrix, the infracted region becomes elongated, may increase in radius of curvature, and may start thinning which involves the process of myocyte "slippage". These changes may cause an immediate increase in the radius of curvature of adjacent border zone myocardium also result in the increase in the border zone wall stress. The cumulative chronic effect of these changes is the stress elevation within the ventricular walls, even in the non-infarcted myocardium. Increased stress, in turn, leads to progressive ventricular dilatation, distortion of ventricular shape, mural hypertrophy and more myocardial stress increase, ultimately causing deterioration of the heart pump function. FIG. 18 shows a summary flowchart illustrating the effects of acute myocardial infarction.

Therapies for treatment of disorders resulting from cardiac remodeling (or complications of remodeling) are highly invasive, risky and expensive, and are commonly only done in conjunction with other procedures (such as heart valve replacement or coronary artery by-pass graft). These procedures are usually done several months or even years after the myocardial infarction when hear is already dilated and functioning poorly. Thus, it would be beneficial to treat myocardial infarction prior to remodeling.

Described herein are methods and devices which may be used for the immediate and early treatment of myocardial infarction. Cardiac rupture post myocardial infarction needs to be treated immediately. The early and rapid appearance of infarct and border zone lengthening and early infarct expansion may be prevented by the early treatments described herein to prevent or attenuate initial myocardial infarct region expansion early after myocardial infarction. These methods and implants may provide an immediate mechanical effect to prevent or attenuate ventricular remodeling, and may also be used in conjunction with therapeutic agents and/or cells to the cardiac endothelium.

SUMMARY OF THE DISCLOSURE

Described herein are methods, devices and systems for treatment the heart following myocardial infarction. In general, these methods typically require the application of a treatment device that supports and/or isolates the infracted region of the heart within about 72 hours of the ischemic event. These methods may be used, for example, to treat a portion of the left ventricle that is affected by myocardial infarction.

In general, a treatment device may be a support device that provides mechanical support to the region of the heart affected by the myocardial infarction, and/or a partitioning device (e.g., including a membrane) that at least partially isolates the region of the heart chamber affected by the myocardial infarction and/or cardiac rupture. In some variations the treatment device is both a support device and a partitioning device.

For example, described herein is a method of preventing cardiac rupture following myocardial infarction comprising delivering a device to a heart chamber exhibiting myocardial infarction within 72 hours of myocardial infarction (wherein the device comprises a reinforced membrane) and deploying the device in the chamber adjacent the region of the chamber wall exhibiting myocardial infarction.

The method may also include the step of identifying the region of the heart chamber exhibiting myocardial infarction. Any appropriate method of identifying the region of the heart chamber exhibiting the myocardial infarction may be used, including visual inspection, electrical inspection, imaging by echocardiography, magnetic resonance or computerized tomography, or the like. For example, electrical inspection may be performed by the use of ECG measurements and analysis, or the use of electrodes on or around the heart tissue. Visual inspection may be done using direct (light) visualization, or by labeling for markers or reactivity. For example, ultrasound may be used to identify region of the heart affected by the myocardial infarction.

As mentioned, a treatment device may include a membrane (e.g., a reinforced membrane). The membrane may be non-porous or porous to allow fluid (including blood) exchange across it. The device may include an expandable frame. The membrane may be attached or connected to the expandable frame. The expandable frame may be formed of an elastic or superelastic material, such as a shape memory material (e.g., Nitinol™, or other superelastic materials). The expandable frame may be formed of a plurality of struts that extend from a hub. The device may also include a foot (e.g., a non-traumatic foot) for contacting the wall of the chamber. In some variations the device is configured so that only minimal (if any) space is partitioned.

The step of delivering the device may include delivering the device in a collapsed configuration. In general, the delivery step may include the step of delivering the device in a collapsed state through a catheter or other inserter. Thus, the device may be held in a first, collapsed or delivery, configuration and may be deployed by expanding into the deployed configuration. The device may be self-expanding, or it may be expanded using a mechanical expander such as a balloon or other structure. Thus, the step of delivering the device may include using a delivery catheter.

When a device is used to treat the heart, the device may be sealed about the periphery of the membrane of the device against the chamber wall of the heart being treated. Any appropriate sealing technique may be used. For example, the device may include a seal region, e.g., an expandable, inflatable, or other region. Examples of devices including a seal are provided herein, and may also be found, for example, in US patent application publication No. 2006/0281965, herein incorporated by reference in its entirety.

The step of deploying the device may therefore also include isolating the region of the chamber wall exhibiting myocardial infarction from the rest of the chamber.

The step of deploying the device may also comprise partitioning the heart chamber into a main productive portion and a secondary non-productive portion, with the region of the chamber exhibiting myocardial infarction or cardiac rupture forming a part of the secondary non-productive portion.

In some variations the treatment device may include anchors or attachments for securing the device to the wall of the heart chamber. For example, the device may include hooks and/or barbs on the membrane and/or expandable frame. Thus, the methods of preventing remodeling due to myocardial infarction may include the step of securing or anchoring the device to the heart wall. In particular, the device may be anchored or secured to the heart wall over the region of myocardial infarction.

One or more therapeutic agents may also be delivered to the heart tissue (e.g., the heart wall) from the device. For example, the device may be coated or impregnated with a therapeutic material. In some variations a therapeutic material is added to the heart chamber after the device is inserted, for example in the space between the device and the heart wall.

Also described herein are methods of preventing cardiac remodeling following myocardial infarction comprising the step of: delivering a device to a left ventricle within 72 hours of myocardial infarction (wherein the device comprises a reinforced membrane) and deploying the device in the left ventricle adjacent a region of the left ventricle exhibiting myocardial infarction.

Also described herein are methods of preventing cardiac remodeling following myocardial infarction. These methods may include delivering a support device to a heart chamber exhibiting myocardial infarction within 72 hours of myocardial infarction (wherein the support device comprises a an expandable frame) and deploying the support device in the chamber adjacent the region of the chamber wall exhibiting myocardial infarction. As mentioned, the method may also include the step of identifying the region of the heart chamber exhibiting myocardial infarction.

The step of delivering the support device may comprise delivering the support device in a collapsed configuration. The support device may be any of the treatment devices described herein; for example, the support devices may be a device having a plurality of struts extending from a central hub. The support device may include a reinforced membrane (which may be impermeable, or permeable, or semi-permeable). The support device may include a foot (e.g., a non-traumatic foot), or a non-traumatic hub.

The step of deploying the support device may include securing the support device to the wall of the chamber. In general, the treatment devices described herein may dynamically flex as the wall of the chamber moves. For example, the support device may be made of a material (e.g., a shape memory alloy) that supports the wall, and flexes as the heart beats.

BRIEF DESCRIPTION OF THE DRAWINGS

FIG. 11 is a transverse cross-sectional view of the delivery system shown in FIG. 10 taken along the lines 11-11.

FIG. 12 is an elevational view, partially in section, of the hub shown in FIG. 7 secured to a helical coil of the delivery system shown in FIG. 10.

FIG. 18 schematically illustrates the effects of myocardial infarction.

FIGS. 19A and 19B is a schematic illustration of a heart in which the implant has been applied.

DETAILED DESCRIPTION

Described herein are methods of treating a patient to prevent or correct cardiac remodeling following myocardial infarction. In general these methods may include inserting or implanting a device in a heart chamber within 72 hours after myocardial infarction, or shortly after a determination of myocardial infarction. The device is preferably placed within the region of the heart chamber exhibiting one or more indication of myocardial infarction. The device may be a support device (e.g., a resilient frame) and/or a partitioning device.

Figure 1A:
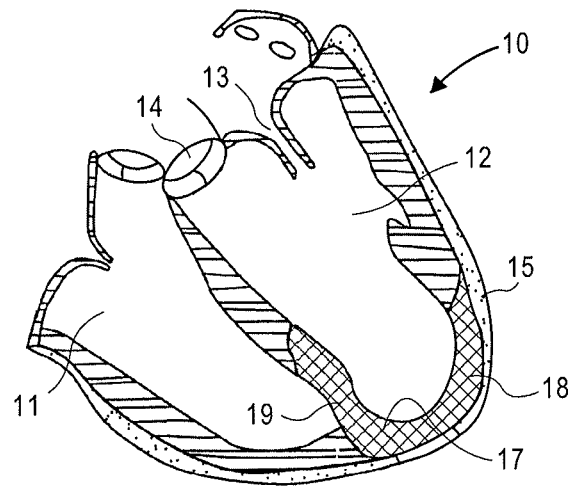
FIG. 1A is a schematic view of a patient's heart having a myocardial infarct.
Figure 1B:
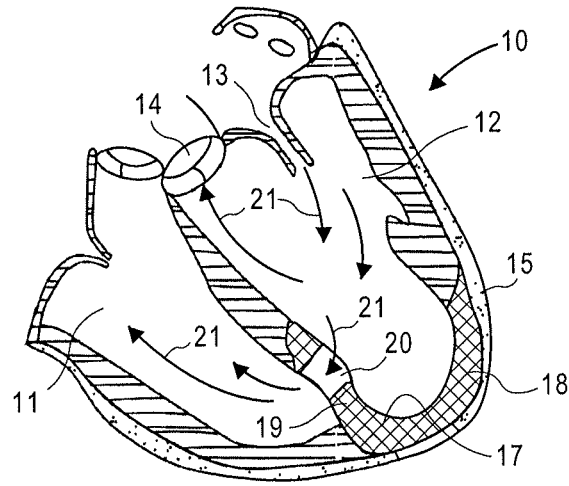
FIG. 1B is a schematic view of the patient's heart of FIG. 1A with a ventricular septal defect resulting from a rupture in the heart wall.

For example, FIG. 1A is a schematic illustration of a patient's heart 10 showing the right ventricle 11 and the left ventricle 12 with the mitral valve 13 and aortic valve 14. A pericardium membrane 15 is shown surrounding the heart 10. At least a portion of myocardium layer 17 of the left ventricle 12, as shown in FIG. 1A, is exhibiting an area of infarct 18 ("MI") extending along a portion of ventricular septum wall 19 which separates the right and left ventricles. This region may exhibit characteristics of an incipient rupture. FIG. 1B illustrates the advancing of the infarct leading to the generation of a rupture or opening 20 in the septum wall 19, a condition referred to as VSD. As shown in FIG. 1B oxygenated blood 21 flows directly to the right ventricle 11 through the septum opening 20. As a result of this movement, or shunting, at least two consequences are reached, firstly, the right portion of the heart works harder pumping a greater volume of blood than it normally would, and secondly, the amount of oxygenated blood in the left ventricle is reduced leading to a lower oxygen level to the other tissues of the body.

Figure 1C:
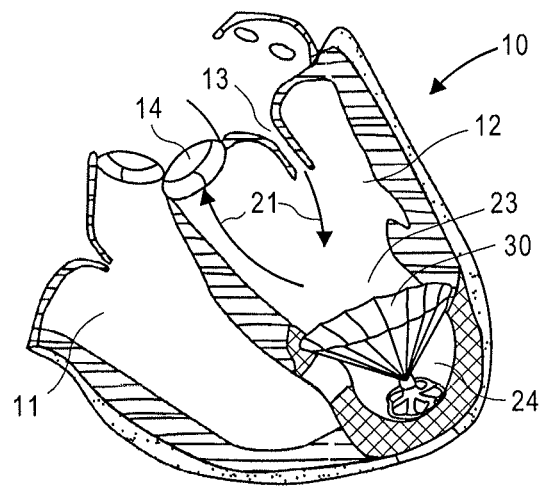
FIG. 1C is a schematic view of the patient's heart of FIG. 1B after treatment following rupture of the heart wall.

In some variations, the heart may be treated after the development of the rupture, as illustrated in FIG. 1C. FIG. 1C illustrates the left ventricle 12 of FIG. 1B after it has been partitioned, with the use of a partitioning device 30 according to the present invention and as described further below, into a main productive or operational portion 23 and a secondary, essentially non-productive portion 24. As can be seen from FIG. 1C, with fluid path to the septum opening blocked or reduced, the normal flow of blood from the left ventricle to the rest of the body through the aortic valve is restored.

Figure 1D:
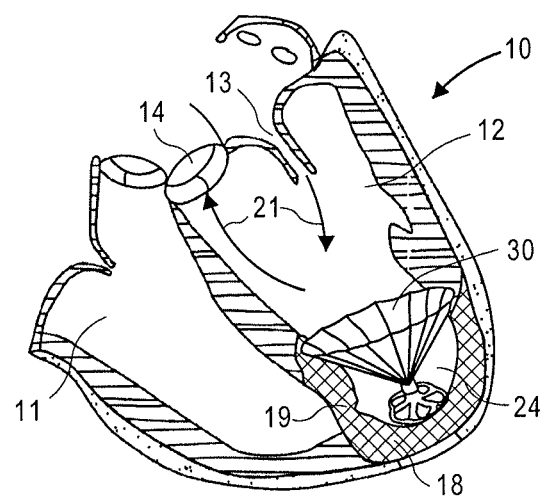
FIG. 1D is a schematic view of the patient's heart after immediate early treatment, as described herein.

In some variations, it may be preferable to treat the heart following myocardial infarction prior to remodeling such as the formation of the rupture shown in FIGS. 1B and 1C. For example, FIG. 1D shows the schematic illustration of the heart of FIG. 1A shortly after determination of a myocardial infarction. The region of the heart chamber exhibiting myocardial infarction (the area of infarct 18) is indicated, and in this example a device 30 has been deployed to reinforce this region. As a part of the method, the device is deployed into the heart chamber adjacent to the region of the heart chamber exhibiting myocardial infarction shortly after a determination of the myocardial infarction has been made. Generally, this occurs prior to substantial remodeling of the heart. For example, this may be less than 72 hours after the myocardial infarction, or less than a few days after the determination of a myocardial infarction.

The occurrence of a myocardial infarction may be determined by any appropriate method, including diagnostics based on physical examination, electrocardiogram, blood (or other tests) for cardiac markers, angiograms, or the like. For example, enzyme markers (e.g., SGOT, LDH, creatine kinase), or other markers (e.g., troponins, glycogen phoshyorylase isoenzyme, myoglobin, etc.) may help determine myocardial infarction. The region of the heart affected by the myocardial infarction may also be determined. For example, visualization techniques (direct or indirect) may be used. For example, angiograms may be used. Other visualization techniques, including scanning (e.g., echocardiography, CT scanning, etc.), electrical mapping, etc. may also be used to localize an area of infarct.

Figure 2A:
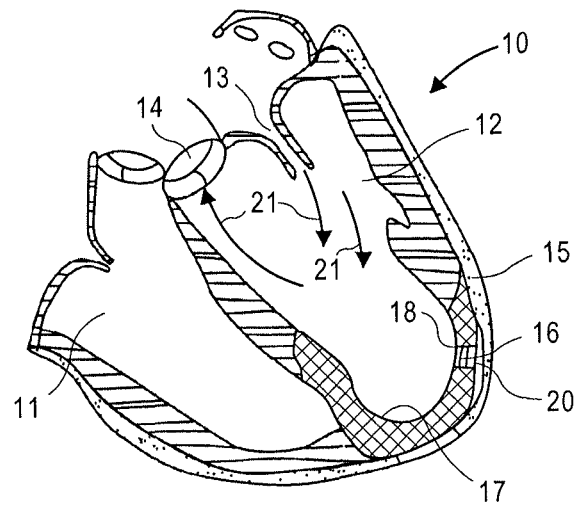
FIG. 2A is a schematic view of a patient's heart exhibiting a myocardial infarct with free wall rupture of the left ventricular chamber.

FIG. 2A is a schematic illustration of a patient's heart 10 showing the right ventricle 11 and the left ventricle 12 with the mitral valve 13 and aortic valve 14. The pericardium membrane 15 is shown surrounding the heart. A pericardium (pericardial complex) consists of an outer fibrous layer and an inner serous layer. The pericardial space 16 normally contains 20-50 mL of fluid. At least a portion of the myocardium layer 17 of the left ventricle 12, as shown in FIG. 2A, is exhibiting an area of infarct 18 ("MI") extending along a portion of the left ventricle 12, which may result in a wall rupture or opening leading to a movement of blood 21 from the left ventricle into the pericardial space 16, as illustrated in FIG. 2B.

Figure 2B:
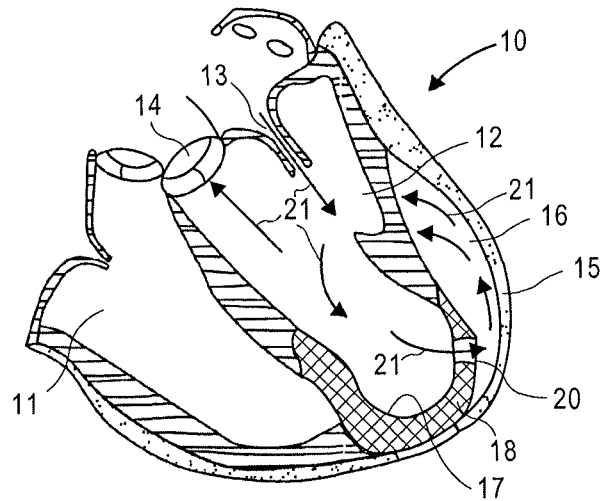
FIG. 2B is a schematic view of the patient's heart of FIG. 2A with a left ventricular chamber tamponade.

FIG. 2B shows the remodeling of the heart following MI. In FIG. 2A the damage from the infarct has advanced, leading to the rupture or opening 20 which is increasing in size. As shown in FIG. 2B, the flow of the blood 21 into the pericardial space 16 increases over time leading to a greater accumulation of blood in the pericardial space. This movement and accumulation of blood in the pericardial space, a condition referred to as ventricular tamponade, results in reduced ventricular filling and subsequent hemodynamic compromise.

Figure 2C:
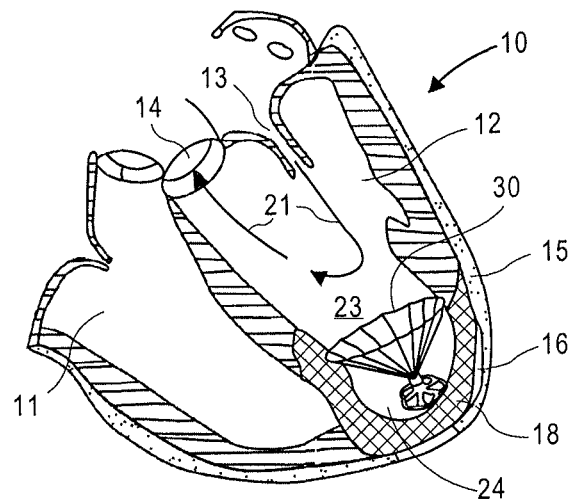
FIG. 2C is a schematic view of the patient's heart of FIG. 2B after treatment following development of tamponade.

This damage may be prevented or reversed by implanting or inserting a support and/or partitioning device, as shown in FIG. 2C. FIG. 2C illustrates the left ventricle 12 of FIG. 2A after a device 30 has been inserted. This device 30 is a partitioning device which both supports the damaged area, and may partition it from other portions of the heart chamber, into the main productive or operational portion 23 and the secondary, essentially non-productive portion 24. As can be seen from 1D and 2C, supporting the damaged region of the heart chamber (e.g., the area of infarct 18), and in some variations partitioning it, may prevent or reverse the remodeling of the heart and help restore the normal flow of blood from the left ventricle to the rest of the body through the aortic valve.

In general, a device for preventing remodeling of the heart comprises a flexible support frame and one or more anchors, and may optionally include one or more of a foot region (e.g., an atraumatic foot region) and a membrane. These treatment device may be referred to as support devices or partitioning devices.

Figure 3:
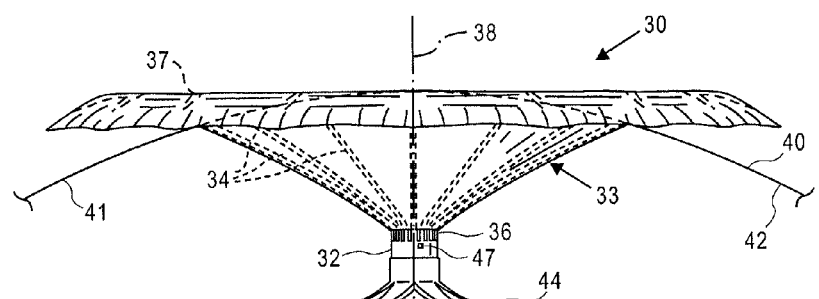
FIG. 3 is an elevational view of a device in an expanded configuration.

FIGS. 3-6 illustrate one example of a device 30 (in this variation a partitioning device) which embodies features of the invention and which may be utilized in practicing the method of the present invention. The device 30 includes a partitioning membrane 31, a hub 32, preferably centrally located on the partitioning device, and a radially expandable reinforcing frame 33 formed of a plurality of ribs 34. Preferably, at least part of the partitioning membrane 31 is secured to a proximal or pressure receiving side 35 of the frame 33 as shown in FIG. 3. The ribs 34 have distal ends 36 which are secured to the hub 32, and free proximal ends 37 which are configured to curve or flare away from a center line axis 38 at least upon expansion of the partitioning device. Radial expansion of the free proximal ends 37 unfurls the membrane 31 secured to the frame 33 so that the membrane presents the pressure receiving surface 35 which defines in part the productive portion 23 of the patient's partitioned heart chamber. A peripheral edge 39 of the membrane 31 may be serrated as shown.

A continuous expansive strand 40 extends around the periphery of the membrane 31 on the pressure receiving side 35 thereof to apply pressure to the pressure side of the flexible material of the membrane to effectively seal the periphery of the membrane against the wall of the ventricular chamber. Ends 41 and 42 of the expansive strand 40 are shown extending away from the device in FIGS. 3 and 5. The ends 41 and 42 may be left unattached or may be secured together, e.g. by a suitable adhesive, to the membrane 31 itself. While not shown in detail, the membrane 31 has a proximal layer secured to the proximal faces of the ribs 34 and a distal layer secured to the distal faces of the ribs in a manner described in co-pending application Ser. No. 10/913,608, filed on Aug. 5, 2004, assigned to the assignee of the present invention, and incorporated herein by reference in its entirety.

Figure 6:
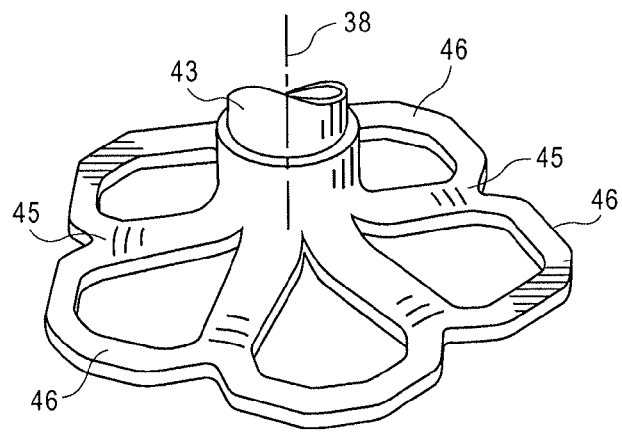
FIG. 6 is a perspective view of a non-traumatic tip of the distally extending stem of the device shown in FIG. 3.
Figure 7:
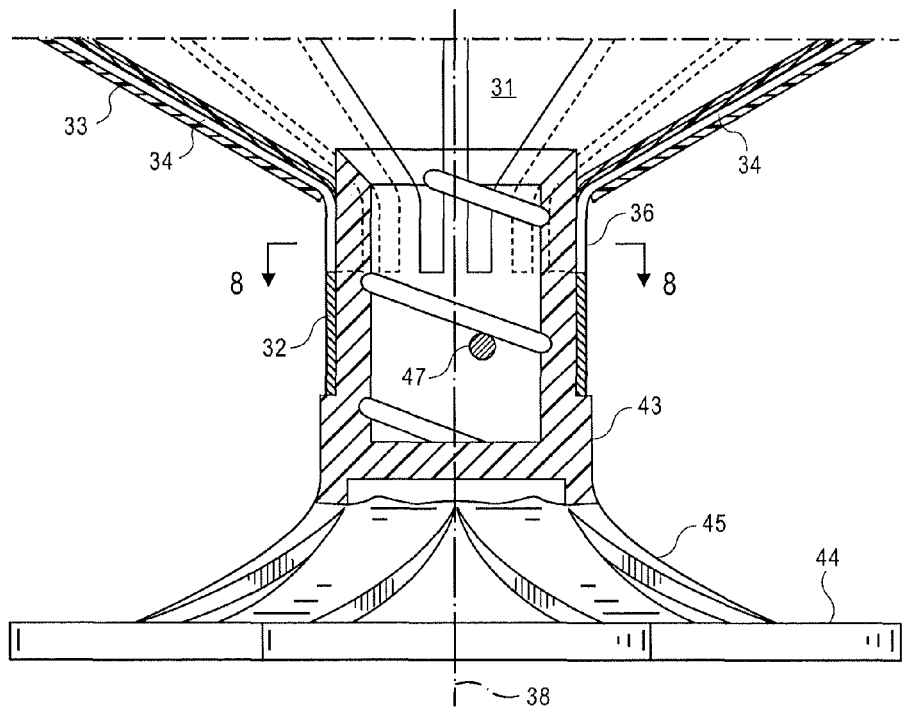
FIG. 7 is a partial cross-sectional view of a hub of the device shown in FIG. 4 taken along the lines 7-7.

The hub 32 shown in FIGS. 6 and 7 preferably has a distally extending stem 43 with a non-traumatic support component 44. The support component 44 has a plurality of pods or feet 45 extending radially away from the center line axis 38 and the ends of the feet 45 are secured to struts 46 which extend between adjacent feet. A plane of material (not shown) may extend between adjacent feet 45 in a web-like fashion to provide further support in addition to or in lieu of the struts 46.

Figure 8:
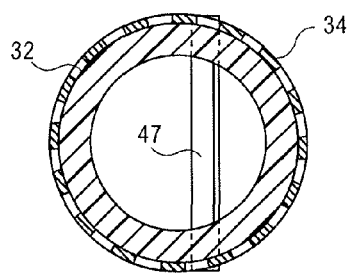
FIG. 8 is a transverse cross-sectional view of the hub shown in FIG. 7 taken along the lines 8-8.
Figure 10:
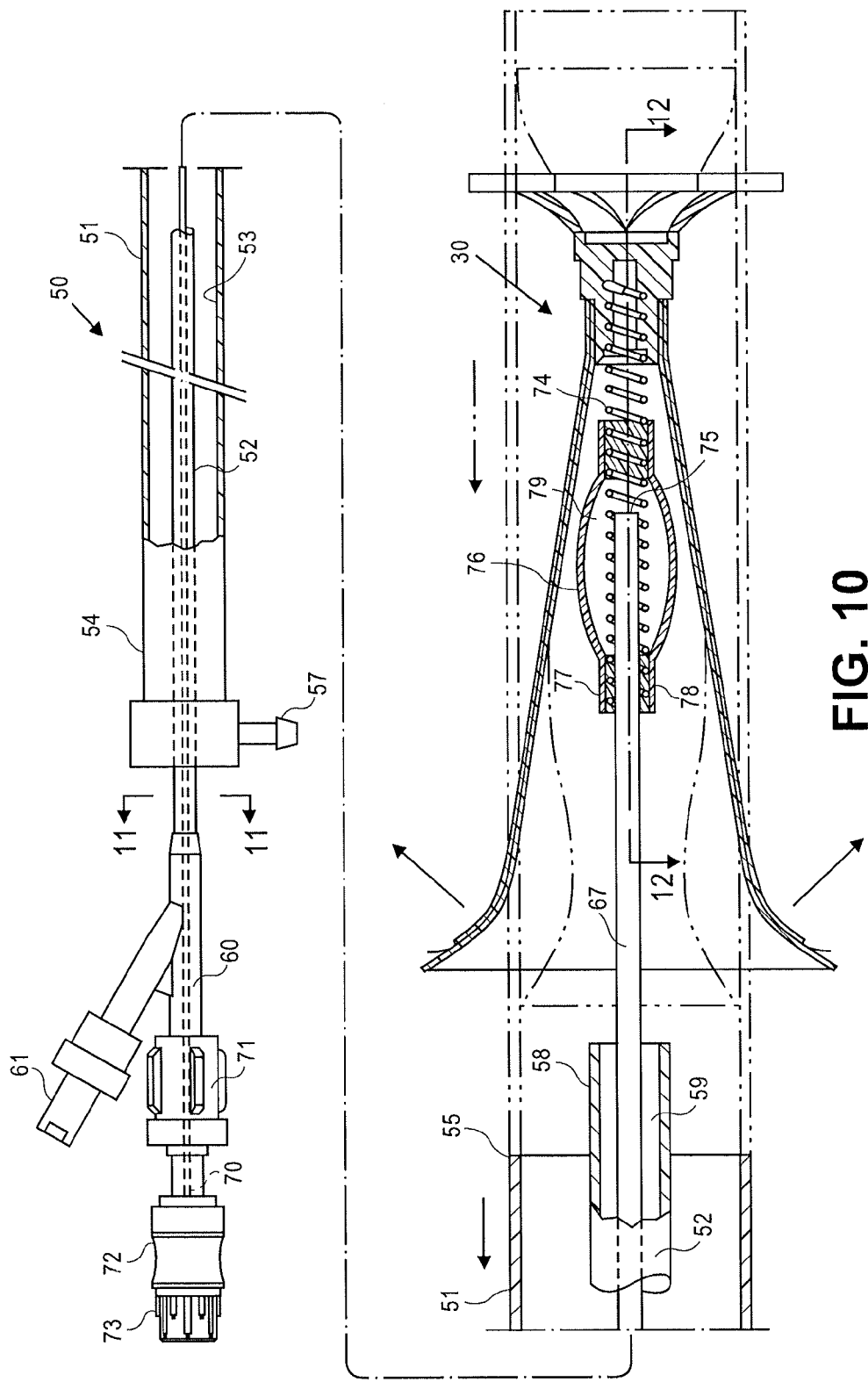
FIG. 10 is a schematic elevational view, partially in section, of a delivery system for a device such as the device shown in FIGS. 3 and 4.

As shown in FIG. 7, the distal ends 36 of the ribs 34 are secured within the hub 32 and, as shown in FIG. 8, a transversely disposed connector bar 47 is secured within the hub which is configured to secure the hub 32 and thus the device 30 to a delivery system such as that shown in FIGS. 10-12.

Figure 9:
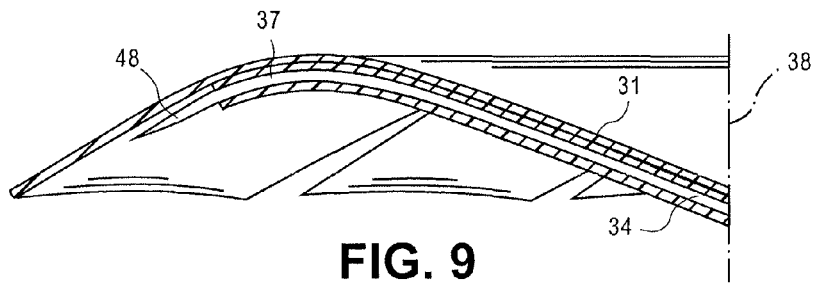
FIG. 9 is a longitudinal view, partially in section of a reinforcing rib and membrane at the periphery of the device shown in FIG. 3.

FIG. 9 illustrates the curved free proximal ends 37 of ribs 34 which are provided with sharp tip elements 48 configured to engage, and preferably penetrate into, the wall of the heart chamber and hold the device 30 in a deployed position within the patient's heart chamber so as to partition the ventricular chamber into a productive portion and a non-productive portion. These sharp tip elements may also be referred to as anchors.

Figure 4:
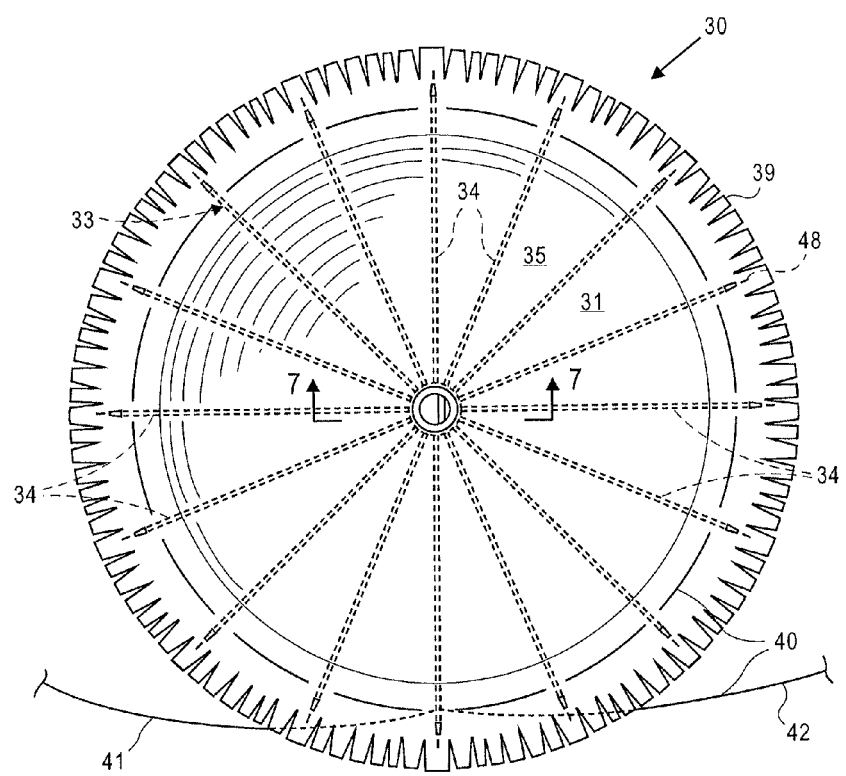
FIG. 4 is a plan view of the device shown in FIG. 3 illustrating the upper surface of the device.
Figure 5:
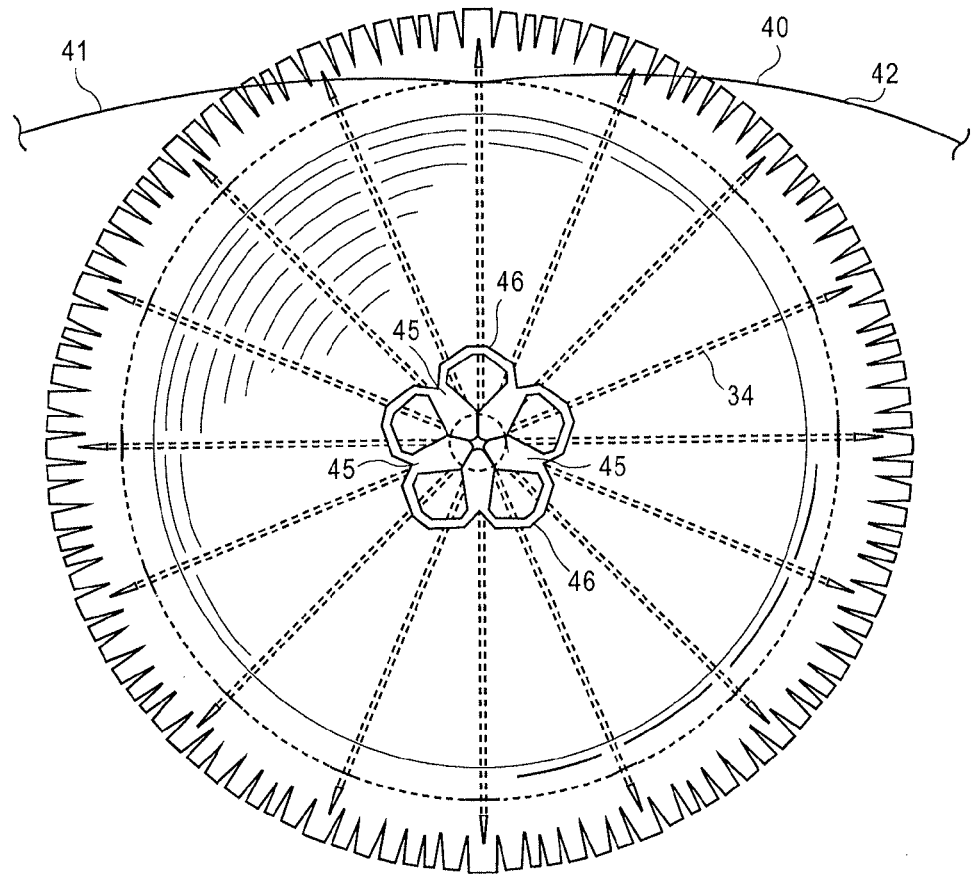
FIG. 5 is a bottom view of the device shown in FIG. 3.

The connector bar 47 of the hub 32, as will be described later, allows the device 30 to be connected to the non-traumatic component 44 which can be secured to a delivery catheter for delivery and to be released from the delivery system within the patient's heart chamber. The distal ends 36 of the reinforcing ribs 34 are secured within the hub 32 in a suitable manner or they may be secured to the surface defining the inner lumen of the hub or they may be disposed within channels or bores in the wall of the hub 32. The distal end 36 of the ribs 34 are pre-shaped so that when the ribs are not constrained, other than by the membrane 31 secured thereto (as shown in FIGS. 3 and 4), the free proximal ends 37 thereof expand to a desired angular displacement, away from the centerline axis 38, of about 20° (degree) to about 90°, preferably about 50° to about 80°. The unconstrained diameter of the device 30 is preferably greater than the diameter of the heart chamber at the deployed location of the device so that an outward force is applied to the wall of the heart chamber by the at least partially expanded ribs 34 during systole and diastole so that the resilient frame 33 augments the heart wall movement.

FIGS. 10-12 illustrate one suitable delivery system 50 delivering a device 30 (e.g., the device shown in FIGS. 3 and 4) into a patient's heart chamber to prevent remodeling of the heart chamber, as illustrated in FIGS. 13A-13E. The delivery system 50 includes a guide catheter 51 and a delivery catheter 52. The present invention may be practiced after the myocardial infarct (e.g., within 72 hours, within 48 hours, etc.), but before remodeling has lead to the creation of rupture or openings (such as 20) in the heart chamber. In some variations, the methods described herein may be used after 72 hours from the myocardial infarction (e.g., within 96 hours, within 120 hours, within 168 hours, within 2 weeks, within 1 month), to minimize the size and/or the effects of remodeling.

The guide catheter 51 has an inner lumen 53 extending between proximal and distal ends, 54 and 55. A flush port 57 on the proximal end 54 of guide catheter 51 is in fluid communication with the inner lumen 53 for injecting therapeutic or diagnostic fluids thereto.

The delivery catheter 52 has an outer shaft 58 with an interior 59, and an adapter 60 at a proximal end thereof with a proximal injection port 61 which is fluid communication with interior 59 for injecting therapeutic or diagnostic fluids thereto. A hemostatic valve (not shown) may be provided at the proximal end 54 of the guide catheter 51 to seal about the outer shaft 58 of the delivery catheter 52.

As shown in more detail in FIG. 11, the outer shaft 58 has an inner shaft 62 with an interior 63, and is disposed within the interior 59 of the outer shaft and is secured to an inner surface 64 of the outer shaft 58 by webs 65 which extend along a substantial length of the inner shaft 62. The webs 65 define in part passageways 66 formed between the inner and outer shafts 62 and 58. The injection port 61 is in fluid communication with passageways 66 for directing therapeutic and/or diagnostic fluids thereto.

A torque shaft 67, preferably formed from hypotubing (e.g., stainless steel or superelastic NiTi) and having an inner lumen 68, is rotatably disposed within an inner lumen 69 of the inner shaft 62, and is secured at a proximal end 70 thereof within an adapter 71 with a rotating knob 72.

A balloon inflation port 73, preferably proximal to the rotating knob 72, is in fluid communication with the inner lumen 68 of the torque shaft 67.

A helical coil screw 74 is secured to a distal end 75 of the torque shaft 67 and rotation of the torque knob 72 on the proximal end 70 of the torque shaft 67 rotates the screw 74 on the distal end 75 of torque shaft 67 to facilitate deployment of the device 30. An inflatable balloon 76 at its proximal end 77 is sealingly secured (e.g., by way of adhesive 78) about the torque shaft 67 proximal to the distal end 75 of the torque shaft and has an interior 79 in fluid communication with the inner lumen 68 of the torque shaft 67. Inflation fluid may be delivered to the interior 79 of the balloon through port 73. Inflation of the balloon 76 by inflation fluid through port 73 facilitates securing the device 30 to the heart wall.

Prior to performing the procedure shown in FIGS. 13A through 13E, the patient may be identified as having recently (e.g., within 72 hours) had a myocardial infarction, by any appropriate method. The region of the heart effected (e.g., the region of the heart chamber effected) may be identified as well. In FIGS. 13A through 13E, the device 30 (a partitioning device in this example) is delivered through the delivery system 50 which includes the guide catheter 51 and the delivery catheter 52. The support or partitioning device 30 is collapsed to a first delivery configuration which has small enough transverse dimensions to be slidably advanced through the inner lumen 53 of the guide catheter 51. Preferably, the guide catheter 51 has been previously percutaneously introduced and advanced through the patent's vasculature, such as the femoral artery, in a conventional manner to the desired heart chamber, such as the left ventricle 12. The delivery catheter 52 with the device 30 attached is advanced through the inner lumen 53 of the guide catheter 51 until the device 30 is ready for deployment from the distal end of the guide catheter 51 into the patient's heart chamber, such as left ventricle 12, to be treated.

Figure 13A:
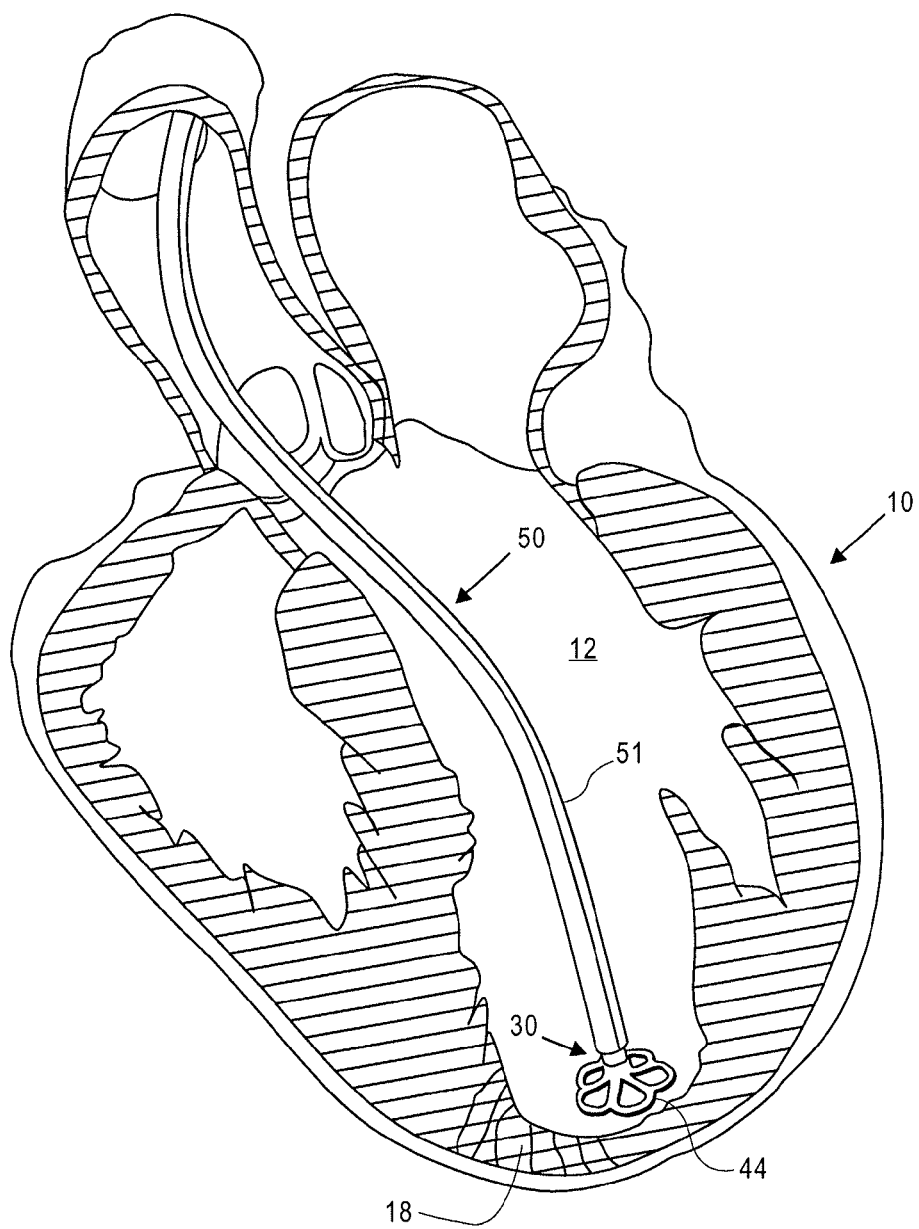
FIGS. 13A-13E are schematic views of a patient's left ventricular chamber illustrating the deployment of the device shown in FIGS. 3 and 4 with the delivery system shown in FIG. 10 to a patient's heart chamber (e.g., left ventricle).
Figure 13B:
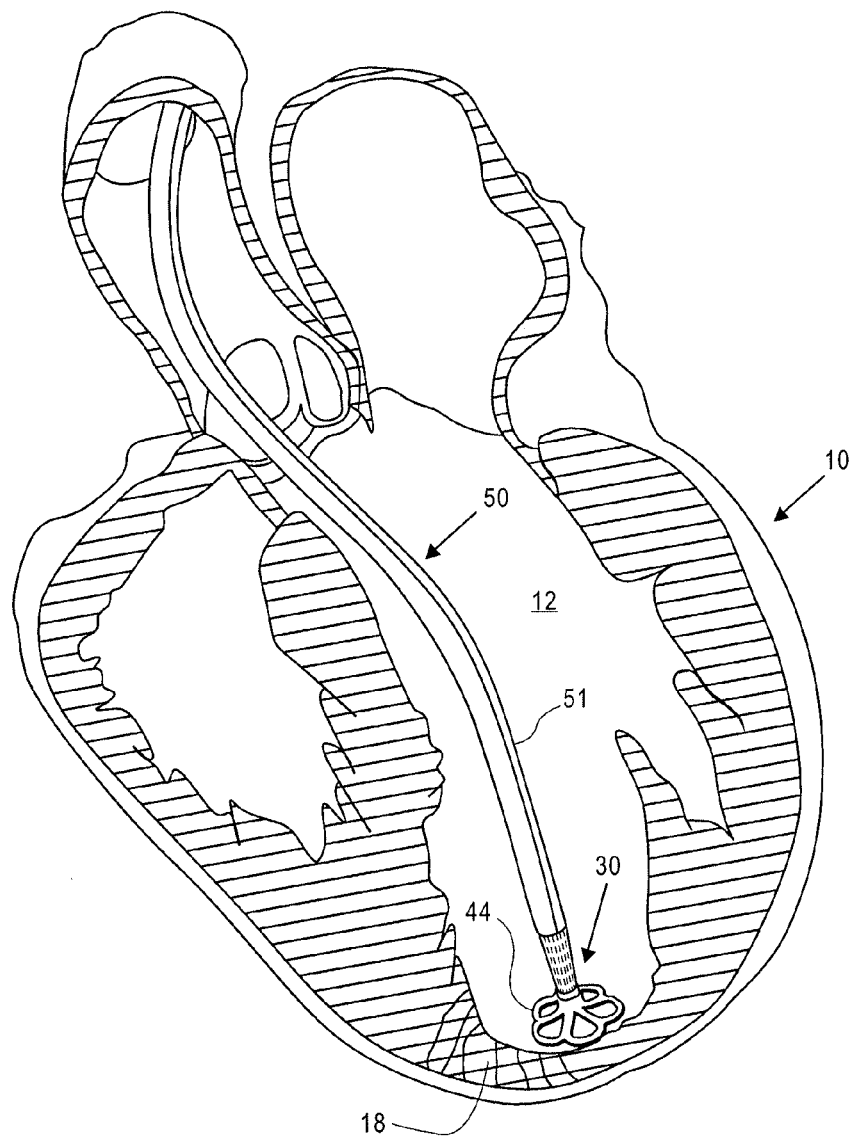
Figure 13C:
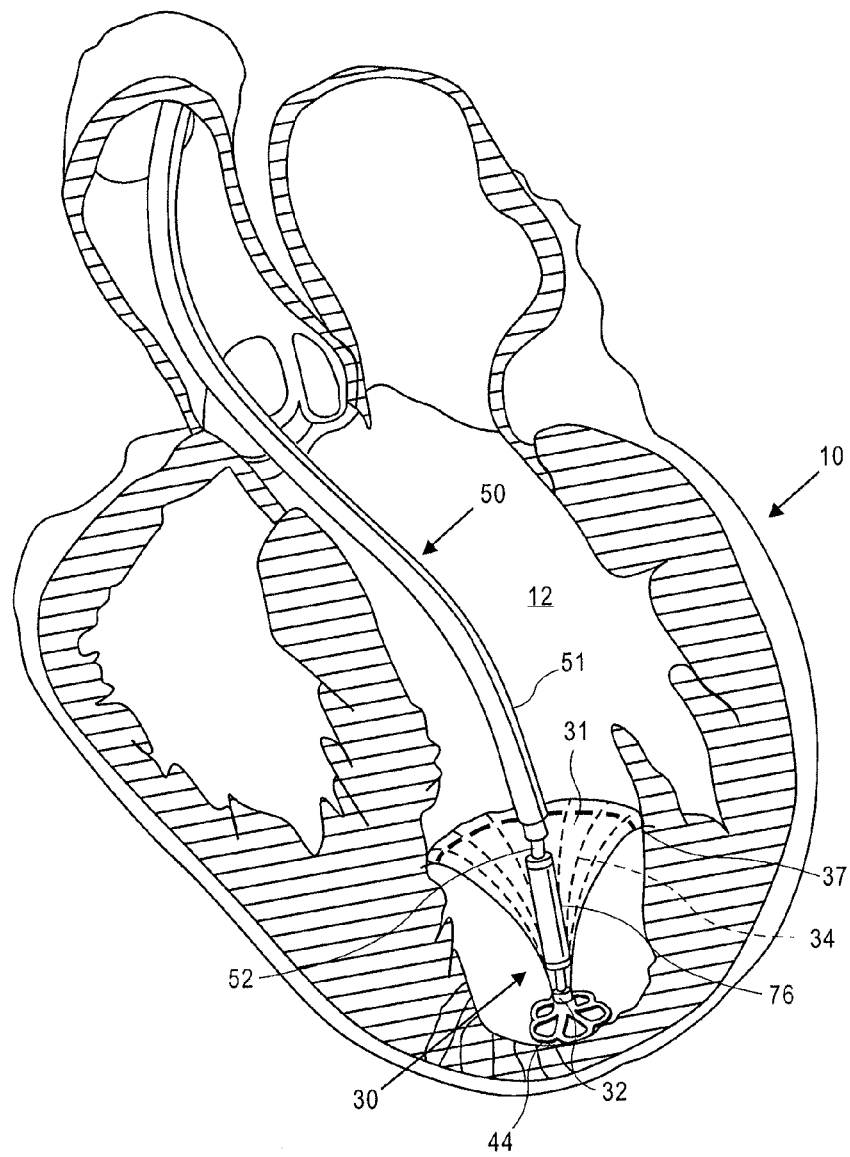
Figure 13D:
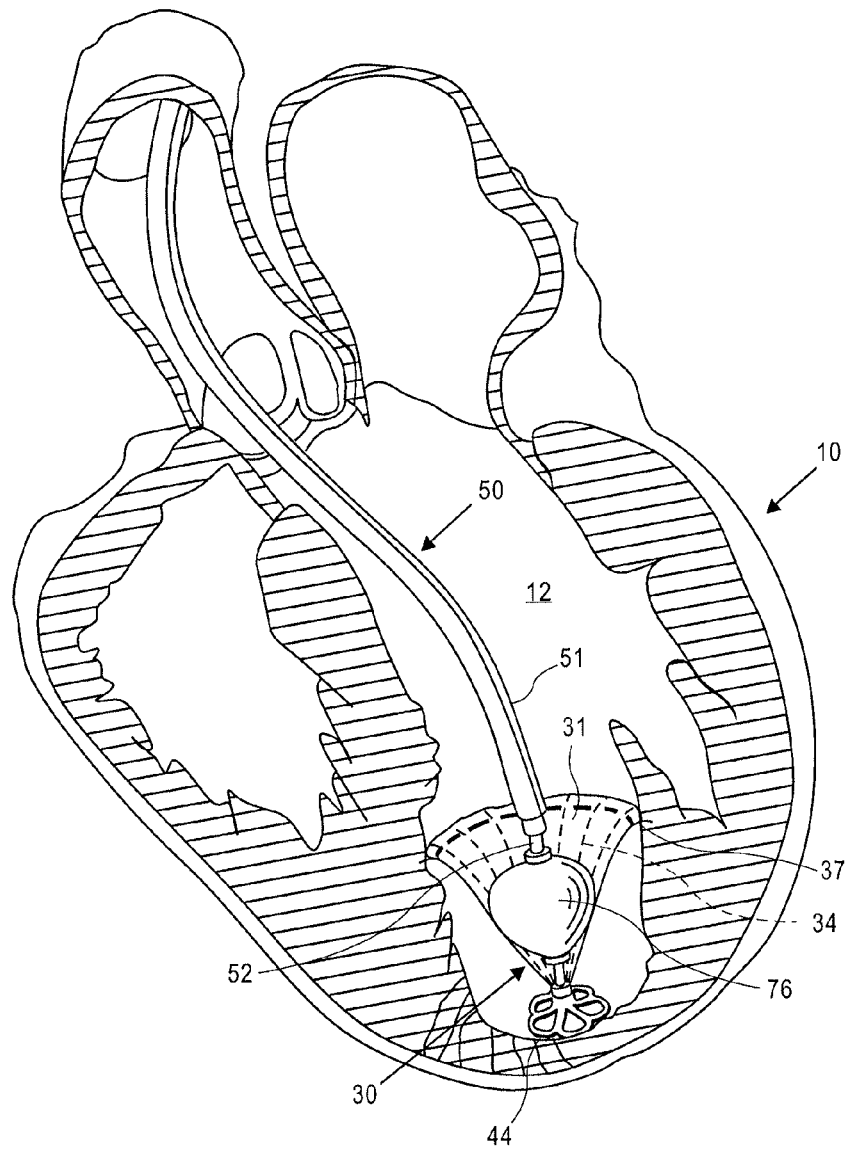
Figure 13E:
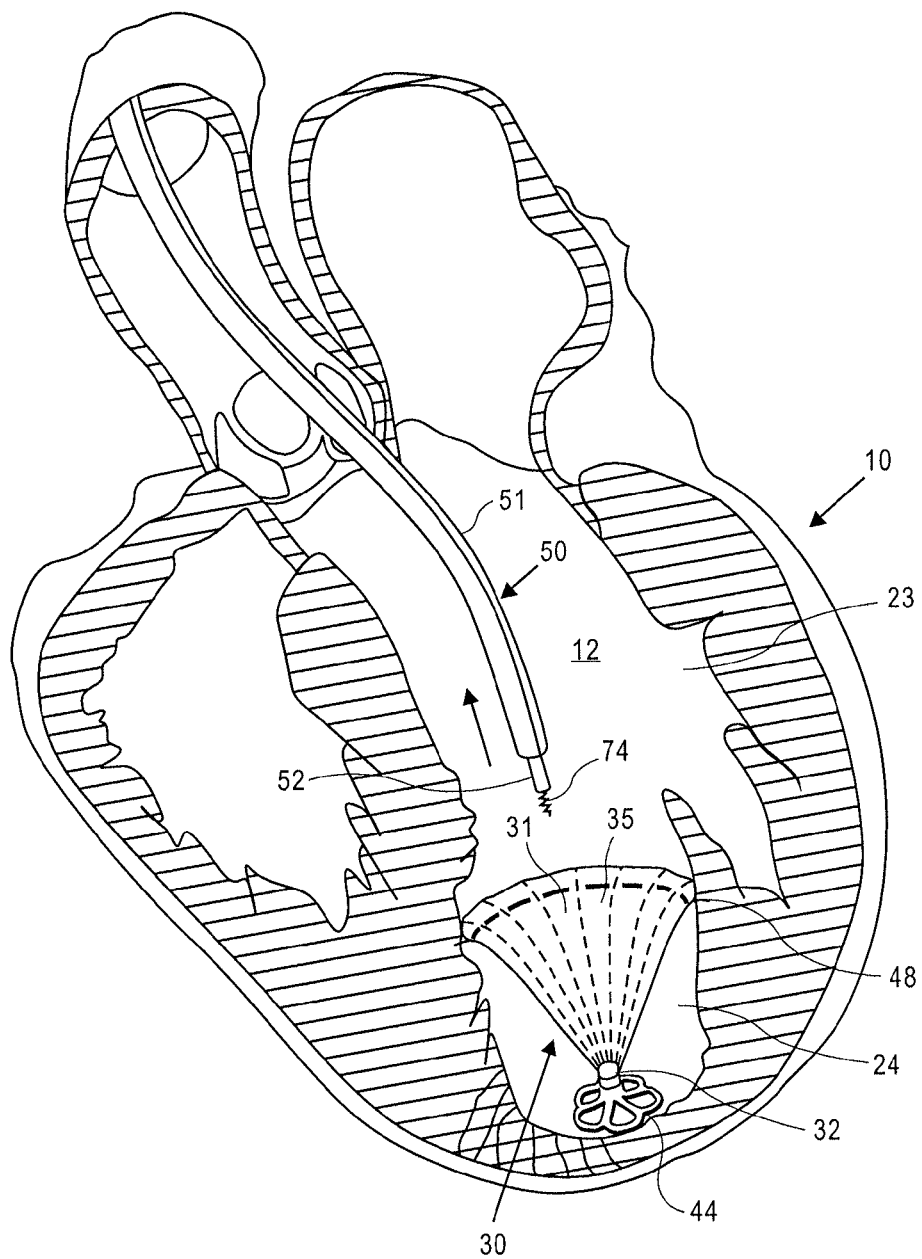

The device 30 mounted on the screw 74 is urged partially out of the inner lumen 53 of the guide catheter 51 until the support component 44 of the hub 32 engages the heart wall as shown in FIG. 13B with the free proximal ends 37 of the ribs 34 in a contracted configuration within the guide catheter. The guiding catheter 51 is withdrawn while the delivery catheter 52 is held in place until the proximal ends 37 of the ribs 34 exit a distal end 55 of the guiding catheter 51. The free proximal ends 37 of ribs 34 expand outwardly to press the sharp proximal tips 48 of the ribs 34 against and preferably into the tissue lining the heart chamber.

With the device deployed within the heart chamber and preferably partially secured therein, inflation fluid is introduced through the inflation port 73 into the inner lumen 68 of the torque shaft 67 and into the balloon interior 79 to inflate the balloon 76. The inflated balloon 76 presses against the pressure receiving surface 35 of the membrane 31 of the device 30 to ensure that the sharp proximal tips 48 are pressed well into the tissue lining the heart chamber. In variations of the device that do not include a membrane, the balloon may expand the frame by pressing against the ribs 34.

With the device 30 properly positioned within the heart chamber, the knob 72 on the torque shaft 67 is rotated (e.g., counter-clockwise) to disengage the helical coil screw 74 of the delivery catheter 52 from the stem 43 of the non-traumatic support component. The counter-clockwise rotation of the torque shaft 67 rotates the helical coil screw 74 which rides in the stem 43 of non-traumatic support component secured within the hub 32. Once the helical coil screw 74 disengages, the stem 43, the delivery system 50, including the guide catheter 51 and the delivery catheter 52, may then be removed from the patient.

In this example, the device 30 partitions the patient's heart chamber, such as left ventricle 12, into the main productive or operational portion 23 and the secondary, essentially non-productive portion 24. The operational portion 23 is much smaller than the original ventricular chamber and provides for an improved ejection fraction. The device may also support the wall of the heart chamber. The partitioning may increase the ejection fraction and provides an improvement in blood flow. Over time, the non-productive portion 24 may fill first with thrombus and subsequently with cellular growth. Bio-resorbable fillers such as polylactic acid, polyglycolic acid, polycaprolactone and copolymers and blends thereof may be employed to initially fill the non-productive portion 24. Fillers may be suitably supplied in a suitable solvent such as dimethylsulfoxide (DMSO). Other materials which accelerate tissue growth or thrombus may be deployed in the non-productive portion 24 as well as non-reactive fillers. It should be noted that although the present figures describe the treatment of the left ventricle, the same can be applied to other chambers of the heart.

Figure 14:
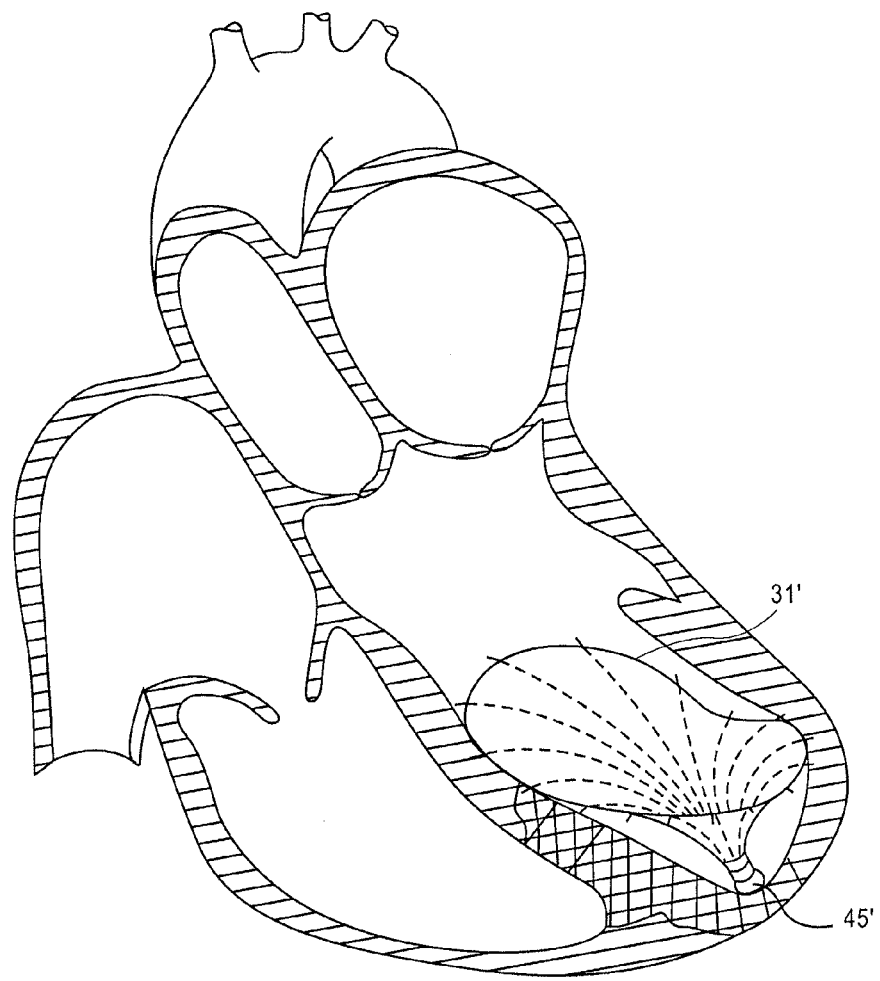
FIG. 14 is a schematic view of the patient's heart after treatment according to a method of the present invention.

FIG. 14 illustrates an alternative design which embodies features of a device usable in practicing methods having features of the present invention, in which the device 30' is provided with an eccentric-shaped membrane 31' which is well suited for treating VSD lesions that may occur further up (more proximal) the ventricular septum because of the different anatomical features and physiologic action of the ventricular septum versus the anterior free wall. The septal wall primarily moves in and out only, relative to the chamber, versus the free wall that has a rotation component to its excursion. Secondly, the outflow track which comprises the upper half of the ventricular septal wall below the aortic valve has very little or no trebeculation. It is particularly well suited for placement of the device placed to address necrotic failure of the tissue of the ventricular septum. In the embodiment shown in FIG. 14, the device is shown with a nubbin foot 45' (and not the extended stem foot) allowing the device to sit more distally and intimately with the apex.

The details of the device 30' shown in FIG. 14 are essentially the same as in the previous embodiments and elements in this alternative embodiment are given the same reference numbers but primed as similar elements in the previously discussed embodiments. The device 30' forms a conical shape as in the previously discussed embodiments but the peripheral base of the conical shape which engages the wall that has a first dimension in a first direction greater than a second dimension in a second direction. Preferably, the second direction is at a right angle with respect to the first direction. The lengths of the ribs 34' are adjusted to provide the desired shape to the periphery of the device which engages the interior of the heart chamber.

Any of the devices described herein (e.g., the devices 30 31') may be conveniently formed by the method described in co-pending application Ser. No. 10/913,608, which is incorporated herein by reference in its entirety.

In variations having a membrane, porous ePTFE materials may be preferred. Alternatively, the membrane 31 may be formed of suitable biocompatible polymeric material which includes Nylon, PET (polyethylene terephthalate) and polyesters such as Hytrel. The membrane 31 is preferably foraminous in nature to facilitate tissue ingrowth after deployment within the patient's heart. The delivery catheter 52 and the guiding catheter 51 may be formed of suitable high strength polymeric material such as PEEK (polyetheretherketone), polycarbonate, PET, Nylon, and the like. Braided composite shafts may also be employed.

Figures 15A, 15B, 15C:
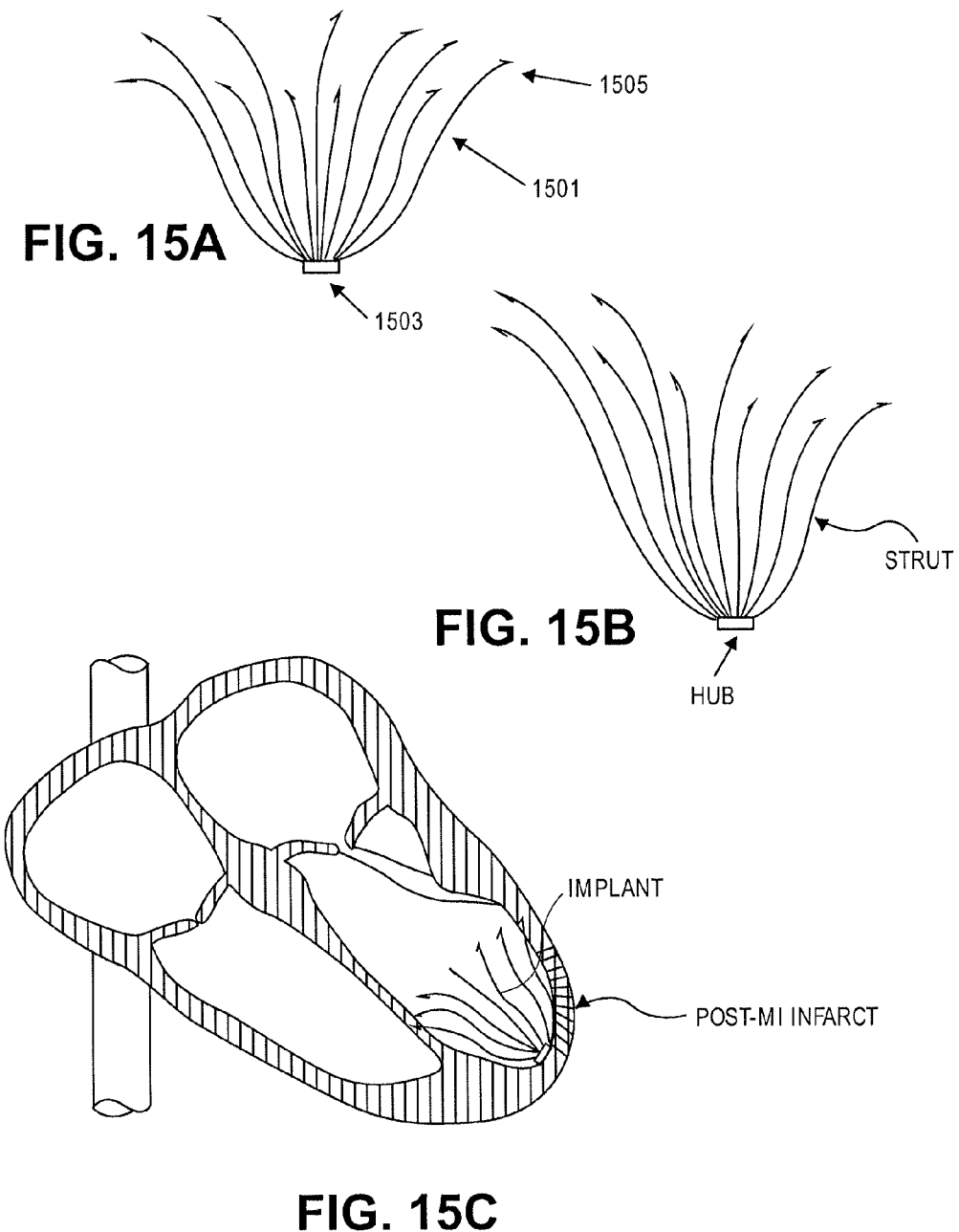
FIG. 15A illustrate one variation of an implant which may be used with the present invention.
FIG. 15B shows another variation of an implant which may be used with the present invention.
FIG. 15C is a schematic view of a heart in which the implant of FIG. 15A has been implanted.

FIGS. 15A through 16B illustrate other variations of devices and methods for using them to prevent remodeling. FIG. 15A sows a device that does not include an occlusive membrane. In this variation of a support device, a plurality of struts 1501 extend from a central hub 1503. The ends of each strut 1501 terminate in an anchor 1505. The struts are typically flexible, and may be collapsed into a delivery configuration and expanded (e.g., self-expanded) into a deployed configuration. The support device shown in FIG. 15B is similar, but has struts of different lengths, similar to the device shown in FIG. 14. FIG. 15C shows a schematic illustration of a heart in which the support device of FIG. 15A has been implanted adjacent a region of the chamber wall exhibiting myocardial infarction. In some variations, the devices may be anchored along the length of the struts rather than, or instead of, just at the ends. In some variations the hub is anchored to the heart chamber wall.

Figure 16A:
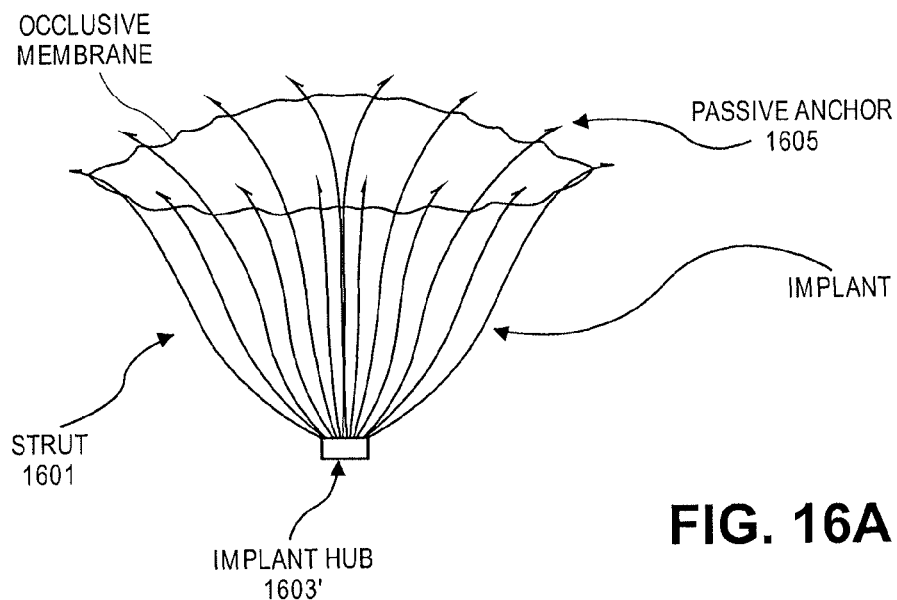
FIG. 16A illustrates another variation of an implant which may be used with the present invention.
Figure 16B:
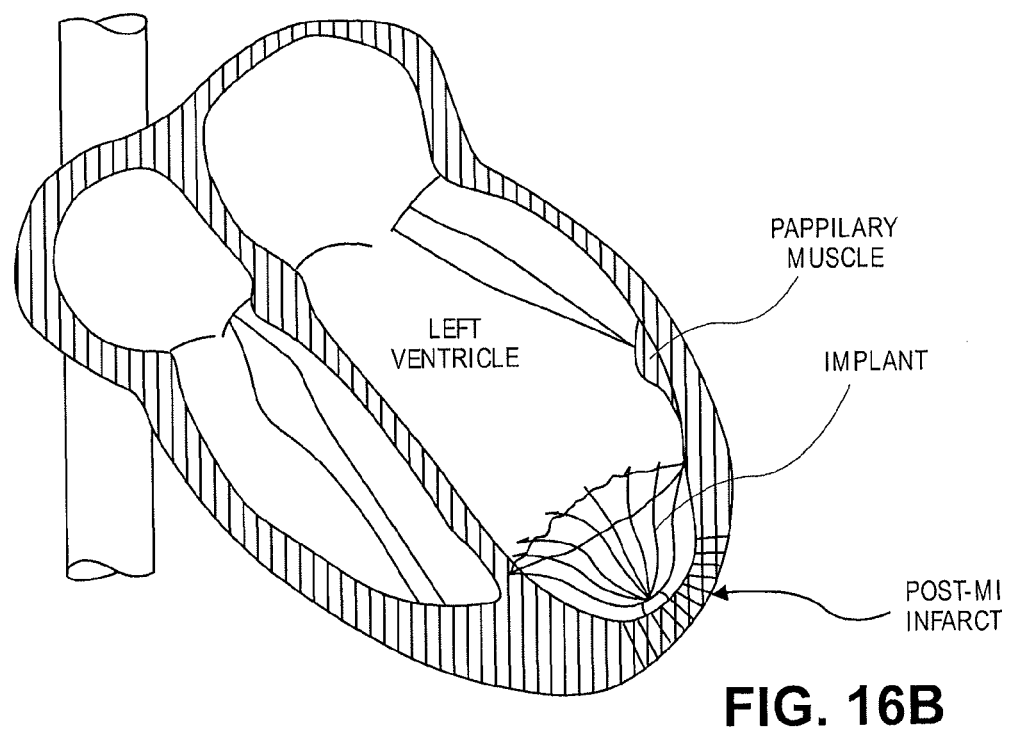
FIG. 16B is a schematic view of a heart in which the implant of FIG. 16A has been implanted.

FIG. 16A shows another variation of an implant, similar to the implant shown in FIG. 3, without the plurality of pods or foot 45. In this example, the hub 1603 may directly contact the wall of the heart chamber. FIG. 16B shows the device of FIG. 16A in the heart.

As mentioned, the implant devices used to treat post-acute myocardial infracted hearts may be configured so that the support framework (e.g., struts) and/or any membrane may be positioned adjacent, contacting, or very close to the wall of the heart. For example, FIGS. 19A and 19B show cross-sectional views of two hears that have devices 1901, 1901' implanted adjacent to the wall in the region affected by the acute myocardial infarction 1903, 1903'.

Figure 17B:
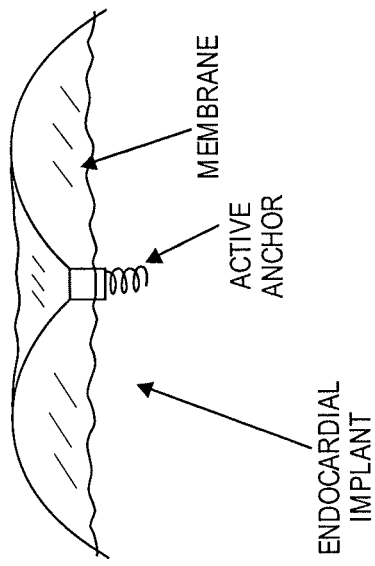
FIGS. 17A and 17B show another variation of an implant which may be used following acute myocardial infarction.
Figure 17A:
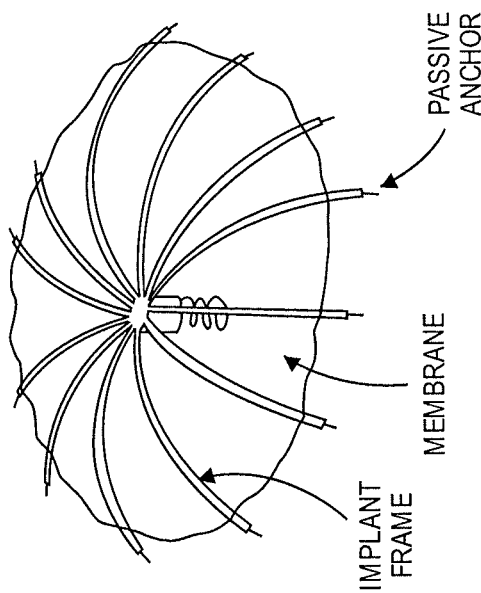

FIGS. 17A and 17B illustrate another variation of a device that may be implanted following acute myocardial infarction in order to prevent cardiac remodeling or damage (configured as an endocardial implant). In this example, the device is configured to be anchored immediately adjacent to the heart wall (e.g., ventricle wall) across from the region of the infarct. The implant includes a frame comprising a plurality of expandable struts which extend from a central hub. The base of the hub in this example includes an anchor ("active anchor") which may be inserted into the heart wall. For example, the hub anchor may be screwed into the heart wall by rotating the device to at least partially penetrate the heart wall and secure the device in place. In addition, the device may also include one or more passive anchors on the struts of the frame, as illustrated. In this variation the struts are at least partially covered by a membrane. The implant sown in FIG. 17A is shown in side cross-section in FIG. 17B.

Figure 17C:
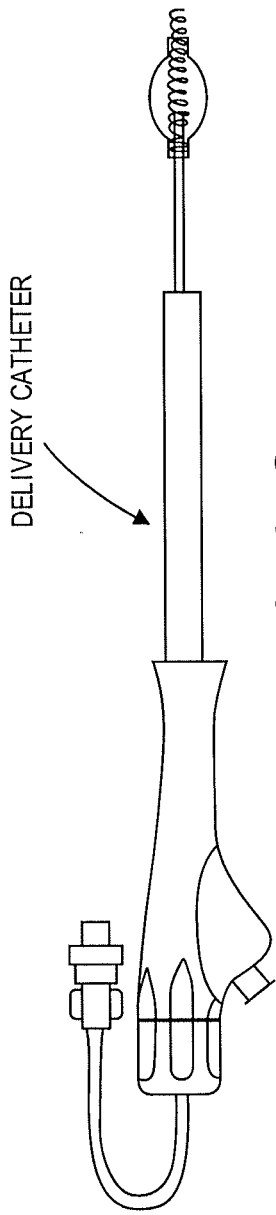
FIGS. 17C and 17D illustrate a delivery system for delivering an implant such as the implant of FIGS. 17A and 17B.
Figure 17D:
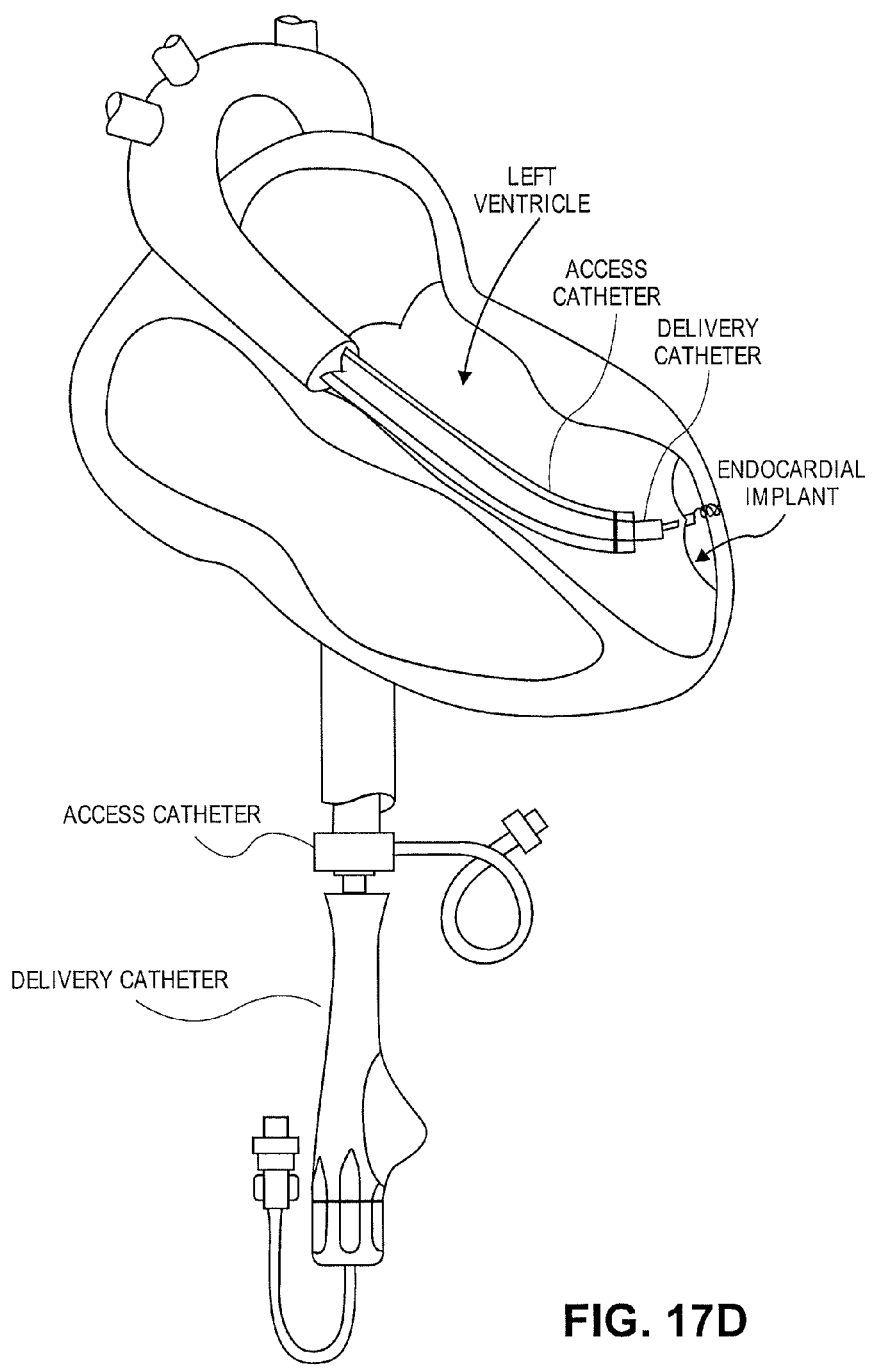

FIG. 17C illustrates one variation of a delivery device for delivering the implant to the heart so that it can be deployed and inserted. For example, the delivery device shown in FIG. 17C includes a delivery catheter having an implant (shown in the collapsed state) at the distal end. FIG. 17D shows the delivery device inserting the implant into the left ventricle of a heart.

To the extent not otherwise described herein, the various components of the devices and delivery systems may be formed of conventional materials and in a conventional manner as will be appreciated by those skilled in the art.

Cardiac endothelium plays an important role in control of the inflammatory response of the myocardium, growth of the heart muscle cells, contractile performance and rhytmicity of the cardiomyocytes. Cardiac endothelial dysfunction has also important role in the pathogenesis of cardiac failure. Therefore, it may be advantageous to selectively deliver therapeutic agents and/or cells to the endothelium in controlled and predictable fashion. The devices (e.g., support device and partitioning devices) described herein may be used to treat disorders by delivering a therapeutic material, including drugs and cells. For example, a frame of a device and/or the membrane of a device can be coated and/or impregnated with a biodegradable coating containing therapeutic agents and deliver these agents to the endothelium. Similarly, a delivery catheter can provide access to infuse various solutions of the therapeutic agents or cells to the area between the devices (e.g., a membrane of the device) and the endothelium, providing precise control of the delivery process to facilitate healing and local regeneration. Any appropriate therapeutic agents may be used, including cytokines, chemokines, inflammatory mediators, growth factors, inotropic agents, anti-arrhythmic agents, other pharmaceutical agents commonly used for treatment post-infarction condition, and various types of cells (myocytes, myoblasts, stem cells).

While particular forms of the invention have been illustrated and described herein, it will be apparent that various modifications and improvements can be made. Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is intended that this invention to be defined by the scope of the appended claims as broadly as the prior art will permit.

Terms such as "element," "member," "component," "device," "section," "portion," "step," "means," and words of similar import, when used herein shall not be construed as invoking the provisions of 35 U.S.C. §112(6) unless the following claims expressly use the term "means" followed by a particular function without specific structure or the term "step" followed by a particular function without specific action. Accordingly, it is not intended that the invention be limited, except as by the appended claims.

What is claimed is:

1. A method for treating a chamber of a patient's heart having a myocardial rupture or septal defect, comprising:
    identifying a region of the chamber of the patient's heart exhibiting the myocardial rupture or septal defect;
    delivering a device having a reinforced membrane to the patient's heart chamber exhibiting the myocardial rupture or septal defect, the device being delivered to the patient's heart chamber in an unexpanded configuration and the reinforced membrane having a distal facing side and a proximal facing side; and
    deploying the device in the chamber of the patient's heart by expanding the device to a deployed configuration within the heart chamber and with the distal facing side of the reinforced membrane facing the region of the chamber of the patient's heart exhibiting the myocardial rupture or septal defect, wherein the device remains entirely within the chamber of the patient's heart; and
    isolating a portion of the chamber having the myocardial rupture or septal defect from a remainder of the chamber.

2. The method of claim 1, wherein the deployed device has a periphery sealed against a chamber wall surface defining in part the chamber of the patient's heart.

3. The method of claim 1, wherein the chamber of the patient's heart is a ventricular chamber.

4. The method of claim 1, wherein the reinforced membrane is configured to isolate the portion of the chamber having the myocardial rupture or septal defect from the rest of the chamber when the device is expanded in a deployed configuration.

5. The method of claim 4, wherein the membrane of the device is formed at least in part of flexible material.

6. The method of claim 5, wherein the device is deployed in the patient's heart chamber so that the flexible material of the device forms a seal about a periphery of the membrane against a ventricular wall surface defining in part the heart chamber.

7. The method of claim 6, wherein the device has an outwardly biased strand which is secured to the periphery of the membrane to seal a peripheral edge of the device to the ventricular wall surface defining in part the heart chamber.

8. The method of claim 1, wherein the step of delivering the device to the patient's heart chamber comprises percutaneously delivering the device to the patient's heart chamber.

9. A method for treating a chamber of a patient's heart having a ventricular rupture or septal defect, comprising:
identifying a region of a ventricle having the ventricular rupture or septal defect;
delivering a partitioning device having a reinforced membrane to a patient's ventricle exhibiting the ventricular rupture or septal defect; and
deploying the partitioning device in the chamber of the patient's ventricle, wherein the reinforced membrane is configured to form a recess in the reinforced membrane when the partitioning device is expanded to a deployed configuration; and
partitioning the heart chamber into a productive portion and a nonproductive portion such that the ventricular rupture or septal defect is located in the nonproductive portion.

10. The method of claim 9, further comprising identifying a region of the ventricle having one or more indicators of myocardial infarction, wherein the ventricular rupture or septal defect is associated with the myocardial infarction.

11. The method of claim 9, further comprising verifying that the ventricular rupture or septal defect is located on an apical portion of the ventricle.

12. The method of claim 9, wherein the partitioning device further comprises a hub with a non-traumatic foot.

13. The method of claim 12, further comprising positioning the non-traumatic foot against an apical portion of the ventricle wall.

14. The method of claim 9, further comprising deploying fillers in the nonproductive portion.

15. The method of claim 14, wherein the fillers are bioresorbable.

16. The method of claim 14, wherein the fillers accelerate thrombosis.

17. The method of claim 14, wherein the fillers accelerate tissue growth.

18. The method of claim 14, wherein the fillers are nonreactive.

19. The method of claim 9, wherein the membrane of the partitioning device is formed at least in part of flexible material.

20. The method of claim 19, wherein the partitioning step further comprises forming a seal about a periphery of the membrane against a ventricular wall surface defining in part the heart chamber.

21. The method of claim 20, wherein the partitioning device has an outwardly biased strand which is secured to the periphery of the membrane to seal a peripheral edge of the partitioning device to the ventricular wall surface defining in part the heart chamber.

22. A method for treating a chamber of a patient's heart having a myocardial rupture or septal defect, comprising:
identifying a region of a heart chamber wall surface exhibiting the myocardial rupture or septal defect;
delivering to the patient's heart chamber exhibiting the myocardial rupture or septal defect a device having a reinforced membrane and an outwardly biased strand secured to a periphery of the reinforced membrane;
deploying the device in the chamber of the patient's heart;
sealing the periphery of the reinforced membrane to the heart chamber wall surface with the outwardly biased strand; and
isolating the region of the chamber having the myocardial rupture or septal defect from a remaining portion of the chamber.

* * * * *